(12) United States Patent
Ito et al.

(10) Patent No.: US 6,825,165 B1
(45) Date of Patent: Nov. 30, 2004

(54) BETACELLULIN MODIFICATION

(75) Inventors: Takashi Ito, Ibaraki (JP); Mitsuyo Kondo, Hyogo (JP); Yoko Tanaka, Kyoto (JP); Masayuki Kobayashi, Hyogo (JP); Koichi Igarashi, Kyoto (JP); Reiko Sasada, Kyoto (JP); Osamu Nishimura, Ibaraki (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/857,815

(22) PCT Filed: Dec. 8, 1999

(86) PCT No.: PCT/JP99/06873

§ 371 (c)(1),
(2), (4) Date: Jun. 8, 2001

(87) PCT Pub. No.: WO00/34478

PCT Pub. Date: Jun. 15, 2000

(30) Foreign Application Priority Data

Dec. 9, 1998 (JP) ............................................ 10/350377
Mar. 3, 1999 (JP) .............................................. 11/55326

(51) Int. Cl.[7] ......................... C07K 14/00; C12N 15/00; A61K 38/00
(52) U.S. Cl. ........................ 514/2; 435/69.1; 435/320.1; 530/300
(58) Field of Search ................................ 530/300, 350; 435/69.1, 320.1, 69.5; 514/2

(56) References Cited

U.S. PATENT DOCUMENTS 6,410,506 B1 * 6/2002 Wei et al. ....................... 514/2

FOREIGN PATENT DOCUMENTS

EP         0 555 785 A1   2/1993   ........... C12N/15/18
WO         WO 97/17086    5/1997

OTHER PUBLICATIONS

B.B.R.C. (1993), entitled: Cloning and Expression of Cdna Encoding Human Betacellulin, A New Member of the EGF Family; Reiko Sasada et al. 190(3), 1173–1179.

Publication Science (1993), entitled: Betacellulin: A Motogen from Pancreatic Cell Tumors, pp 259 (5101), 1604–1607.

J.Cell. Physiol. (1995), entitled: Carboxyl–Terminal Truncation of Leucine 76 Converts Heparin–Binding EGF–Like Growth Factor from a Heparin–Enhancible to a Heparin–Suppressible Growth Factor, 163 (2), 407–417.

Publication by Gibbes R. Johnson et al, entitled: Characterization of High and Low Molecular Weight Forms of Amphiregulin that Differ in Glycosylation and Peptide Core Length, J. Biol. Chem. (1993), 268(25), 18835–18843.

Japanese application, by Itaru Kojima, entitled: Differentiation of Pancreatic Endocrine Cells, Diabetes J. (1998), 26(3), 97–103 and translation thereof.

Publication entitled: Recombinant Human Betacellulin, by Tatsuya Watanabe et al., J. Biol. Chem (1994), 269 (13), 9969–9973.

Publication entitled: The Chemical Synthesis and Biological Activity of EGF–Like Domain of Betacellulin, A New Member of EGF Family, By Song Yub Shin, et al., Peptide Chemistry (1994), 1993, 225–228.

Publication entitled: Betacellulun–Pseudomonas Toxin Fusion Proteins Bind but are not Cytotoxic to Cells Expressing HER4; Correlation of EGFR for Cytotoxic Activity, Oncogene (1998), 16(9), 1209–1215.

Miyagawa et al., "Betacellulin accelerates the β cell neogenesis, and improves glucose intolerance in diabetic mice", Abstracts of the 1997 Japan Diabetes Association Conference, 125.

* cited by examiner

*Primary Examiner*—Elizabeth Kemmerer
*Assistant Examiner*—Regina M. DeBerry
(74) *Attorney, Agent, or Firm*—Edwards & Angell, LLP; David G. Conlin; Jennifer K. Rosenfield

(57) ABSTRACT

The betacellulin mutein or its salt of the present invention is useful for better therapeutic drug for diabetes. Since they have intact BTC activity and reduced EGF activity, and no antigenicity-related problems.

6 Claims, 10 Drawing Sheets

No addition of betacellulin

Met-80 residue betacellulin

Met-77 residue betacellulin

Met-76 residue betacellulin

SEQUENCE LISTING

<160> NUMBER OF SEQ ID NOS: 64

<210> SEQ ID NO 1
<211> LENGTH: 77
<212> TYPE: PRT
<213> ORGANISM: Human

<400> SEQUENCE: 1

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val Asp
65                  70                  75

<210> SEQ ID NO 2
<211> LENGTH: 76
<212> TYPE: PRT
<213> ORGANISM: Human

<400> SEQUENCE: 2

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val
65                  70                  75

<210> SEQ ID NO 3
<211> LENGTH: 47
<212> TYPE: PRT
<213> ORGANISM: Human

<400> SEQUENCE: 3

Arg Lys Gly His Phe Ser Arg Cys Pro Lys Gln Tyr Lys His Tyr Cys
1               5                   10                  15

Ile Lys Gly Arg Cys Arg Phe Val Val Ala Glu Gln Thr Pro Ser Cys
            20                  25                  30

-continued

```
Val Cys Asp Glu Gly Tyr Ile Gly Ala Arg Cys Glu Arg Val Asp
        35                  40                  45

<210> SEQ ID NO 4
<211> LENGTH: 46
<212> TYPE: PRT
<213> ORGANISM: Human

<400> SEQUENCE: 4

Arg Lys Gly His Phe Ser Arg Cys Pro Lys Gln Tyr Lys His Tyr Cys
 1               5                  10                  15

Ile Lys Gly Arg Cys Arg Phe Val Val Ala Glu Gln Thr Pro Ser Cys
             20                  25                  30

Val Cys Asp Glu Gly Tyr Ile Gly Ala Arg Cys Glu Arg Val
        35                  40                  45

<210> SEQ ID NO 5
<211> LENGTH: 79
<212> TYPE: PRT
<213> ORGANISM: Artificial sequence
<220> FEATURE:
<223> OTHER INFORMATION: amino acid sequence of betacellulin mutein
      (BTC 1-76, 78-80)

<400> SEQUENCE: 5

Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
             20                  25                  30

Gly His Phe Ser Arg Cys Pro Lys Gln Tyr Lys His Tyr Cys Ile Lys
         35                  40                  45

Gly Arg Cys Arg Phe Val Val Ala Glu Gln Thr Pro Ser Cys Val Cys
     50                  55                  60

Asp Glu Gly Tyr Ile Gly Ala Arg Cys Glu Arg Val Leu Phe Tyr
65                  70                  75

<210> SEQ ID NO 6
<211> LENGTH: 78
<212> TYPE: PRT
<213> ORGANISM: Artificial sequence
<220> FEATURE:
<223> OTHER INFORMATION: amino acid sequence of betacellulin mutein
      (BTC 1-76, 78, 79)

<400> SEQUENCE: 6

Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
             20                  25                  30

Gly His Phe Ser Arg Cys Pro Lys Gln Tyr Lys His Tyr Cys Ile Lys
         35                  40                  45

Gly Arg Cys Arg Phe Val Val Ala Glu Gln Thr Pro Ser Cys Val Cys
     50                  55                  60

Asp Glu Gly Tyr Ile Gly Ala Arg Cys Glu Arg Val Leu Phe
65                  70                  75

<210> SEQ ID NO 7
<211> LENGTH: 77
<212> TYPE: PRT
<213> ORGANISM: Artificial sequence
<220> FEATURE:
<223> OTHER INFORMATION: amino acid sequence of betacellulin mutein
```

(BTC 1-76, 78)

<400> SEQUENCE: 7

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val Leu
65                  70                  75

<210> SEQ ID NO 8
<211> LENGTH: 79
<212> TYPE: PRT
<213> ORGANISM: Artificial sequence
<220> FEATURE:
<223> OTHER INFORMATION: amino acid sequence of betacellulin mutein
      (BTC 1-77, 79, 80)

<400> SEQUENCE: 8

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val Asp Phe Tyr
65                  70                  75

<210> SEQ ID NO 9
<211> LENGTH: 78
<212> TYPE: PRT
<213> ORGANISM: Artificial sequence
<220> FEATURE:
<223> OTHER INFORMATION: amino acid sequence of betacellulin mutein
      (BTC 1-77, 80)

<400> SEQUENCE: 9

Asp Gly Asn Ser Thr Arg Ser Pro Glu Thr Asn Gly Leu Leu Cys Gly
1               5                   10                  15

Asp Pro Glu Glu Asn Cys Ala Ala Thr Thr Gln Ser Lys Arg Lys
            20                  25                  30

Gly His Phe Ser Arg Cys Pro Lys Gln Tyr Lys His Tyr Cys Ile Lys
        35                  40                  45

Gly Arg Cys Arg Phe Val Val Ala Glu Gln Thr Pro Ser Cys Val Cys
    50                  55                  60

Asp Glu Gly Tyr Ile Gly Ala Arg Cys Glu Arg Val Asp Phe
65                  70                  75

<210> SEQ ID NO 10
<211> LENGTH: 49
<212> TYPE: PRT
<213> ORGANISM: Artificial sequence
<220> FEATURE:
<223> OTHER INFORMATION: amino acid sequence of betacellulin mutein
      (BTC 31-76, 78-80)

-continued

```
<400> SEQUENCE: 10

Arg Lys Gly His Phe Ser Arg Cys Pro Lys Gln Tyr Lys His Tyr Cys
1               5                   10                  15

Ile Lys Gly Arg Cys Arg Phe Val Val Ala Glu Gln Thr Pro Ser Cys
            20                  25                  30

Val Cys Asp Glu Gly Tyr Ile Gly Ala Arg Cys Glu Arg Val Leu Phe
        35                  40                  45

Tyr

<210> SEQ ID NO 11
<211> LENGTH: 48
<212> TYPE: PRT
<213> ORGANISM: Artificial sequence
<220> FEATURE:
<223> OTHER INFORMATION: amino acid sequence of betacellulin mutein
      (BTC 31-76, 78, 79)

<400> SEQUENCE: 11

Arg Lys Gly His Phe Ser Arg Cys Pro Lys Gln Tyr Lys His Tyr Cys
1               5                   10                  15

Ile Lys Gly Arg Cys Arg Phe Val Val Ala Glu Gln Thr Pro Ser Cys
            20                  25                  30

Val Cys Asp Glu Gly Tyr Ile Gly Ala Arg Cys Glu Arg Val Leu Phe
        35                  40                  45

<210> SEQ ID NO 12
<211> LENGTH: 47
<212> TYPE: PRT
<213> ORGANISM: Artificial sequence
<220> FEATURE:
<223> OTHER INFORMATION: amino acid sequence of betacellulin mutein
      (BTC 31-76, 78)

<400> SEQUENCE: 12

Arg Lys Gly His Phe Ser Arg Cys Pro Lys Gln Tyr Lys His Tyr Cys
1               5                   10                  15

Ile Lys Gly Arg Cys Arg Phe Val Val Ala Glu Gln Thr Pro Ser Cys
            20                  25                  30

Val Cys Asp Glu Gly Tyr Ile Gly Ala Arg Cys Glu Arg Val Leu
        35                  40                  45

<210> SEQ ID NO 13
<211> LENGTH: 49
<212> TYPE: PRT
<213> ORGANISM: Artificial sequence
<220> FEATURE:
<223> OTHER INFORMATION: amino acid sequence of betacellulin mutein
      (BTC 31-77, 79, 80)

<400> SEQUENCE: 13

Arg Lys Gly His Phe Ser Arg Cys Pro Lys Gln Tyr Lys His Tyr Cys
1               5                   10                  15

Ile Lys Gly Arg Cys Arg Phe Val Val Ala Glu Gln Thr Pro Ser Cys
            20                  25                  30

Val Cys Asp Glu Gly Tyr Ile Gly Ala Arg Cys Glu Arg Val Asp Phe
        35                  40                  45

Tyr

<210> SEQ ID NO 14
<211> LENGTH: 48
```

```
<212> TYPE: PRT
<213> ORGANISM: Artificial sequence
<220> FEATURE:
<223> OTHER INFORMATION: amino acid sequence of betacellulin mutein
      (BTC 31-77, 79)

<400> SEQUENCE: 14

Arg Lys Gly His Phe Ser Arg Cys Pro Lys Gln Tyr Lys His Tyr Cys
 1               5                  10                  15
Ile Lys Gly Arg Cys Arg Phe Val Val Ala Glu Gln Thr Pro Ser Cys
                20                  25                  30
Val Cys Asp Glu Gly Tyr Ile Gly Ala Arg Cys Glu Arg Val Asp Phe
            35                  40                  45

<210> SEQ ID NO 15
<211> LENGTH: 231
<212> TYPE: DNA
<213> ORGANISM: Human

<400> SEQUENCE: 15
gatgggaatt ccaccagaag tcctgaaact aatggcctcc tctgtggaga ccctgaggaa      60
aactgtgcag ctaccaccac acaatcaaag cggaaaggcc acttctctag gtgccccaag     120
caatacaagc attactgcat caaagggaga tgccgcttcg tggtggccga gcagacgccc     180
tcctgtgtct gtgatgaagg ctacattgga gcaaggtgtg agagagttga c              231

<210> SEQ ID NO 16
<211> LENGTH: 228
<212> TYPE: DNA
<213> ORGANISM: Human

<400> SEQUENCE: 16
gatgggaatt ccaccagaag tcctgaaact aatggcctcc tctgtggaga ccctgaggaa      60
aactgtgcag ctaccaccac acaatcaaag cggaaaggcc acttctctag gtgccccaag     120
caatacaagc attactgcat caaagggaga tgccgcttcg tggtggccga gcagacgccc     180
tcctgtgtct gtgatgaagg ctacattgga gcaaggtgtg agagagtt                  228

<210> SEQ ID NO 17
<211> LENGTH: 141
<212> TYPE: DNA
<213> ORGANISM: Human

<400> SEQUENCE: 17
cggaaaggcc acttctctag gtgccccaag caatacaagc attactgcat caaagggaga      60
tgccgcttcg tggtggccga gcagacgccc tcctgtgtct gtgatgaagg ctacattgga     120
gcaaggtgtg agagagttga c                                               141

<210> SEQ ID NO 18
<211> LENGTH: 138
<212> TYPE: DNA
<213> ORGANISM: Human

<400> SEQUENCE: 18
cggaaaggcc acttctctag gtgccccaag caatacaagc attactgcat caaagggaga      60
tgccgcttcg tggtggccga gcagacgccc tcctgtgtct gtgatgaagg ctacattgga     120
gcaaggtgtg agagagtt                                                   138

<210> SEQ ID NO 19
```

-continued

```
<211> LENGTH: 237
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 5

<400> SEQUENCE: 19
gatgggaatt ccaccagaag tcctgaaact aatggcctcc tctgtggaga ccctgaggaa      60
aactgtgcag ctaccaccac acaatcaaag cggaaaggcc acttctctag gtgccccaag    120
caatacaagc attactgcat caaagggaga tgccgcttcg tggtggccga gcagacgccc    180
tcctgtgtct gtgatgaagg ctacattgga gcaaggtgtg agagagttttt gttttac      237

<210> SEQ ID NO 20
<211> LENGTH: 234
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 6

<400> SEQUENCE: 20
gatgggaatt ccaccagaag tcctgaaact aatggcctcc tctgtggaga ccctgaggaa      60
aactgtgcag ctaccaccac acaatcaaag cggaaaggcc acttctctag gtgccccaag    120
caatacaagc attactgcat caaagggaga tgccgcttcg tggtggccga gcagacgccc    180
tcctgtgtct gtgatgaagg ctacattgga gcaaggtgtg agagagtttt gttt          234

<210> SEQ ID NO 21
<211> LENGTH: 231
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 7

<400> SEQUENCE: 21
gatgggaatt ccaccagaag tcctgaaact aatggcctcc tctgtggaga ccctgaggaa      60
aactgtgcag ctaccaccac acaatcaaag cggaaaggcc acttctctag gtgccccaag    120
caatacaagc attactgcat caaagggaga tgccgcttcg tggtggccga gcagacgccc    180
tcctgtgtct gtgatgaagg ctacattgga gcaaggtgtg agagagtttt g             231

<210> SEQ ID NO 22
<211> LENGTH: 237
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 8

<400> SEQUENCE: 22
gatgggaatt ccaccagaag tcctgaaact aatggcctcc tctgtggaga ccctgaggaa      60
aactgtgcag ctaccaccac acaatcaaag cggaaaggcc acttctctag gtgccccaag    120
caatacaagc attactgcat caaagggaga tgccgcttcg tggtggccga gcagacgccc    180
tcctgtgtct gtgatgaagg ctacattgga gcaaggtgtg agagagttga cttttac       237

<210> SEQ ID NO 23
<211> LENGTH: 234
<212> TYPE: DNA
<213> ORGANISM: Artificial sequence
```

```
<220> FEATURE:
<223> OTHER INFORMATION: base sequence of cDNA encoding betacellulin
      mutein represented by SEQ ID NO: 9

<400> SEQUENCE: 23
gatgggaatt ccaccagaag tcctgaaact aatggcctcc tctgtggaga ccctgaggaa      60
aactgtgcag ctaccaccac acaatcaaag cggaaaggcc acttctctag gtgccccaag    120
caatacaagc attactgcat caaagggaga tgccgcttcg tggtggccga gcagacgccc    180
tcctgtgtct gtgatgaagg ctacattgga gcaaggtgtg agagagttga cttt          234

<210> SEQ ID NO 24
<211> LENGTH: 147
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 10

<400> SEQUENCE: 24
cggaaaggcc acttctctag gtgccccaag caatacaagc attactgcat caaagggaga     60
tgccgcttcg tggtggccga gcagacgccc tcctgtgtct gtgatgaagg ctacattgga    120
gcaaggtgtg agagagtttt gttttac                                        147

<210> SEQ ID NO 25
<211> LENGTH: 144
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 11

<400> SEQUENCE: 25
cggaaaggcc acttctctag gtgccccaag caatacaagc attactgcat caaagggaga     60
tgccgcttcg tggtggccga gcagacgccc tcctgtgtct gtgatgaagg ctacattgga    120
gcaaggtgtg agagagtttt gttt                                           144

<210> SEQ ID NO 26
<211> LENGTH: 141
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 12

<400> SEQUENCE: 26
cggaaaggcc acttctctag gtgccccaag caatacaagc attactgcat caaagggaga     60
tgccgcttcg tggtggccga gcagacgccc tcctgtgtct gtgatgaagg ctacattgga    120
gcaaggtgtg agagagtttt g                                              141

<210> SEQ ID NO 27
<211> LENGTH: 147
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 13

<400> SEQUENCE: 27
cggaaaggcc acttctctag gtgccccaag caatacaagc attactgcat caaagggaga     60
tgccgcttcg tggtggccga gcagacgccc tcctgtgtct gtgatgaagg ctacattgga    120
```

```
gcaaggtgtg agagagttga cttttac                                          147

<210> SEQ ID NO 28
<211> LENGTH: 144
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 14

<400> SEQUENCE: 28
cggaaaggcc acttctctag gtgccccaag caatacaagc attactgcat caaagggaga     60
tgccgcttcg tggtggccga gcagacgccc tcctgtgtct gtgatgaagg ctacattgga    120
gcaaggtgtg agagagttga cttt                                           144

<210> SEQ ID NO 29
<211> LENGTH: 31
<212> TYPE: DNA
<213> ORGANISM: Artificial Sequence
<220> FEATURE:
<223> OTHER INFORMATION: Primer 1

<400> SEQUENCE: 29
catatggatg ggaattccac cagaagtcct g                                    31

<210> SEQ ID NO 30
<211> LENGTH: 33
<212> TYPE: DNA
<213> ORGANISM: Artificial Sequence
<220> FEATURE:
<223> OTHER INFORMATION: Primer 2

<400> SEQUENCE: 30
ggatccctag tcaactctct cacaccttgc tcc                                  33

<210> SEQ ID NO 31
<211> LENGTH: 24
<212> TYPE: DNA
<213> ORGANISM: Artificial Sequence
<220> FEATURE:
<223> OTHER INFORMATION: Primer RI-1

<400> SEQUENCE: 31
agagtcaagg atcccccaac cact                                            24

<210> SEQ ID NO 32
<211> LENGTH: 22
<212> TYPE: DNA
<213> ORGANISM: Artificial Sequence
<220> FEATURE:
<223> OTHER INFORMATION: Primer RI-3

<400> SEQUENCE: 32
agctggtcac ttagggctgg gg                                              22

<210> SEQ ID NO 33
<211> LENGTH: 26
<212> TYPE: DNA
<213> ORGANISM: Artificial Sequence
<220> FEATURE:
<223> OTHER INFORMATION: Primer RI-1Cla

<400> SEQUENCE: 33
gaatcgatag agtcaaggat ccccca                                          26
```

-continued

<210> SEQ ID NO 34
<211> LENGTH: 22
<212> TYPE: DNA
<213> ORGANISM: Artificial Sequence
<220> FEATURE:
<223> OTHER INFORMATION: Primer RI-3Xho

<400> SEQUENCE: 34
gactcgagct ggtcacttag gg                                             22

<210> SEQ ID NO 35
<211> LENGTH: 80
<212> TYPE: PRT
<213> ORGANISM: Human

<400> SEQUENCE: 35

Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
             20                  25                  30

Gly His Phe Ser Arg Cys Pro Lys Gln Tyr Lys His Tyr Cys Ile Lys
         35                  40                  45

Gly Arg Cys Arg Phe Val Val Ala Glu Gln Thr Pro Ser Cys Val Cys
     50                  55                  60

Asp Glu Gly Tyr Ile Gly Ala Arg Cys Glu Arg Val Asp Leu Phe Tyr
 65                  70                  75                  80

<210> SEQ ID NO 36
<211> LENGTH: 240
<212> TYPE: DNA
<213> ORGANISM: Human

<400> SEQUENCE: 36
gatgggaatt ccaccagaag tcctgaaact aatggcctcc tctgtggaga ccctgaggaa     60
aactgtgcag ctaccaccac acaatcaaag cggaaaggcc acttctctag gtgccccaag    120
caatacaagc attactgcat caaagggaga tgccgcttcg tggtggccga gcagacgccc    180
tcctgtgtct gtgatgaagg ctacattgga gcaaggtgtg agagagttga cttgttttac    240

<210> SEQ ID NO 37
<211> LENGTH: 75
<212> TYPE: PRT
<213> ORGANISM: Human

<400> SEQUENCE: 37

Gly Asn Ser Thr Arg Ser Pro Glu Thr Asn Gly Leu Leu Cys Gly Asp
 1               5                  10                  15

Pro Glu Glu Asn Cys Ala Ala Thr Thr Thr Gln Ser Lys Arg Lys Gly
             20                  25                  30

His Phe Ser Arg Cys Pro Lys Gln Tyr Lys His Tyr Cys Ile Lys Gly
         35                  40                  45

Arg Cys Arg Phe Val Val Ala Glu Gln Thr Pro Ser Cys Val Cys Asp
     50                  55                  60

Glu Gly Tyr Ile Gly Ala Arg Cys Glu Arg Val
 65                  70                  75

<210> SEQ ID NO 38
<211> LENGTH: 53
<212> TYPE: PRT

<213> ORGANISM: Human

<400> SEQUENCE: 38

```
Ala Thr Thr Thr Gln Ser Lys Arg Lys Gly His Phe Ser Arg Cys Pro
 1               5                   10                  15
Lys Gln Tyr Lys His Tyr Cys Ile Lys Gly Arg Cys Arg Phe Val Val
            20                  25                  30
Ala Glu Gln Thr Pro Ser Cys Val Cys Asp Glu Gly Tyr Ile Gly Ala
        35                  40                  45
Arg Cys Glu Arg Val
    50          53
```

<210> SEQ ID NO 39
<211> LENGTH: 30
<212> TYPE: DNA
<213> ORGANISM: Artificial Sequence
<220> FEATURE:
<223> OTHER INFORMATION: Primer 3

<400> SEQUENCE: 39
cagcatatgg ggaattccac cagaagtcct                               30

<210> SEQ ID NO 40
<211> LENGTH: 34
<212> TYPE: DNA
<213> ORGANISM: Artificial Sequence
<220> FEATURE:
<223> OTHER INFORMATION: Primer 4

<400> SEQUENCE: 40
ggatccctaa actctctcac accttgctcc aatg                          34

<210> SEQ ID NO 41
<211> LENGTH: 30
<212> TYPE: DNA
<213> ORGANISM: Artificial Sequence
<220> FEATURE:
<223> OTHER INFORMATION: Primer 5

<400> SEQUENCE: 41
cagcatatgg ctaccaccac acaatcaaag                               30

<210> SEQ ID NO 42
<211> LENGTH: 225
<212> TYPE: DNA
<213> ORGANISM: Human

<400> SEQUENCE: 42
gggaattcca ccagaagtcc tgaaactaat ggcctcctct gtggagaccc tgaggaaaac    60
tgtgcagcta ccaccacaca atcaaagcgg aaaggccact tctctaggtg ccccaagcaa   120
tacaagcatt actgcatcaa agggagatgc cgcttcgtgg tggccgagca gacgccctcc   180
tgtgtctgtg atgaaggcta cattggagca aggtgtgaga gagtt                  225

<210> SEQ ID NO 43
<211> LENGTH: 159
<212> TYPE: DNA
<213> ORGANISM: Human

<400> SEQUENCE: 43
cctaccacca cacaatcaaa ccccaaaccc cacttctcta cctcccccaa ccaatacaac    60
cattactcca tcaaacccac atccccttc ctcctccccc accacacccc ctcctctctc   120
tctcatcaac cctacattcc accaacctct cacacactt         159

<210> SEQ ID NO 44
<211> LENGTH: 53
<212> TYPE: PRT
<213> ORGANISM: Artificial sequence
<220> FEATURE:
<223> OTHER INFORMATION: amino acid sequence of betacwelluin mutein
      (BTC 31-58, Asn, Pro, Ser, 59-80)

<400> SEQUENCE: 44

Arg Lys Gly His Phe Ser Arg Cys Pro Lys Gln Tyr Lys His Tyr Cys
                 5                  10                  15

Ile Lys Gly Arg Cys Arg Phe Val Val Ala Glu Gln Asn Pro Ser Thr
             20                  25                  30

Pro Ser Cys Val Cys Asp Glu Gly Tyr Ile Gly Ala Arg Cys Glu Arg
         35                  40                  45

Val Asp Leu Phe Tyr
     50

<210> SEQ ID NO 45
<211> LENGTH: 48
<212> TYPE: PRT
<213> ORGANISM: Artificial sequence
<220> FEATURE:
<223> OTHER INFORMATION: amino acid sequence of betacwelluin mutein
      (Asn, Ser, Asp, Ser, Glu, BTC38-80)

<400> SEQUENCE: 45

Asn Ser Asp Ser Glu Cys Pro Lys Gln Tyr Lys His Tyr Cys Ile Lys
                 5                  10                  15

Gly Arg Cys Arg Phe Val Val Ala Glu Gln Thr Pro Ser Cys Val Cys
             20                  25                  30

Asp Glu Gly Tyr Ile Gly Ala Arg Cys Glu Arg Val Asp Leu Phe Tyr
         35                  40                  45

<210> SEQ ID NO 46
<211> LENGTH: 83
<212> TYPE: PRT
<213> ORGANISM: Artificial sequence
<220> FEATURE:
<223> OTHER INFORMATION: amino acid sequence of betacwelluin mutein
      (BTC 1-58, Asn, Pro, Ser, 59-80)

<400> SEQUENCE: 46

Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
             20                  25                  30

Gly His Phe Ser Arg Cys Pro Lys Gln Tyr Lys His Tyr Cys Ile Lys
         35                  40                  45

Gly Arg Cys Arg Phe Val Val Ala Glu Gln Asn Pro Ser Thr Pro Ser
     50                  55                  60

Cys Val Cys Asp Glu Gly Tyr Ile Gly Ala Arg Cys Glu Arg Val Asp
65                   70                  75                  80

Leu Phe Tyr

<210> SEQ ID NO 47
<211> LENGTH: 249
<212> TYPE: DNA
<213> ORGANISM: Artificial sequence

```
<220> FEATURE:
<223> OTHER INFORMATION: base sequence of cDNA encoding betacellulin
      mutein represented by SEQ ID NO: 46

<400> SEQUENCE: 47
gatgggaatt ccaccagaag tcctgaaact aatggcctcc tctgtggaga ccctgaggaa    60
aactgtgcag ctaccaccac acaatcaaag cggaaaggcc acttctctag gtgccccaag   120
caatacaagc attactgcat caagggaga tgccgcttcg tggtggccga gcagaacccc    180
tcgacgccct cctgtgtctg tgatgaaggc tacattggag caaggtgtga gagagttgac   240
ttgttttac                                                           249

<210> SEQ ID NO 48
<211> LENGTH: 159
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 44

<400> SEQUENCE: 48
cggaaaggcc acttctctag gtgccccaag caatacaagc attactgcat caaagggaga    60
tgccgcttcg tggtggccga gcagaacccc tcgacgccct cctgtgtctg tgatgaaggc   120
tacattggag caaggtgtga gagagttgac ttgttttac                          159

<210> SEQ ID NO 49
<211> LENGTH: 144
<212> TYPE: DNA
<213> ORGANISM: Artificial sequence
<220> FEATURE:
<223> OTHER INFORMATION: base sequence of cDNA encoding betacellulin
      mutein represented by SEQ ID NO: 45

<400> SEQUENCE: 49
aacagcgact ctgagtgccc caagcaatac aagcattact gcatcaaagg gagatgccgc    60
ttcgtggtgg ccgagcagac gccctcctgt gtctgtgatg aaggctacat tggagcaagg   120
tgtgagagag ttgacttgtt ttac                                          144

<210> SEQ ID NO 50
<211> LENGTH: 30
<212> TYPE: DNA
<213> ORGANISM: Artificial Sequence
<220> FEATURE:
<223> OTHER INFORMATION: Primer BT-95h

<400> SEQUENCE: 50
agcatatgcg gaaaggccac ttctctaggt                                     30

<210> SEQ ID NO 51
<211> LENGTH: 30
<212> TYPE: DNA
<213> ORGANISM: Artificial Sequence
<220> FEATURE:
<223> OTHER INFORMATION: Primer BT-94h

<400> SEQUENCE: 51
ctggatccta gtaaaacaag tcaactctct                                     30

<210> SEQ ID NO 52
<211> LENGTH: 30
<212> TYPE: DNA
<213> ORGANISM: Artificial Sequence
```

```
<220> FEATURE:
<223> OTHER INFORMATION: Primer PET-1

<400> SEQUENCE: 52
gaaataattt tgtttaactt taagaaggag                              30

<210> SEQ ID NO 53
<211> LENGTH: 30
<212> TYPE: DNA
<213> ORGANISM: Artificial Sequence
<220> FEATURE:
<223> OTHER INFORMATION: Primer BTC-1

<400> SEQUENCE: 53
aggagggcgt cgagggttc tgctcggcca                               30

<210> SEQ ID NO 54
<211> LENGTH: 30
<212> TYPE: DNA
<213> ORGANISM: Artificial Sequence
<220> FEATURE:
<223> OTHER INFORMATION: Primer BTC-2

<400> SEQUENCE: 54
tggccgagca gaaccctcg acgccctcct                               30

<210> SEQ ID NO 55
<211> LENGTH: 30
<212> TYPE: DNA
<213> ORGANISM: Artificial Sequence
<220> FEATURE:
<223> OTHER INFORMATION: Primer BTC-3

<400> SEQUENCE: 55
tctatgcgca cccgttctcg gagcactgtc                              30

<210> SEQ ID NO 56
<211> LENGTH: 35
<212> TYPE: DNA
<213> ORGANISM: Artificial Sequence
<220> FEATURE:
<223> OTHER INFORMATION: Primer BTC-7

<400> SEQUENCE: 56
tatacatatg aacagcgact ctgagtgccc caagc                        35

<210> SEQ ID NO 57
<211> LENGTH: 40
<212> TYPE: PRT
<213> ORGANISM: Human

<400> SEQUENCE: 57

Asp Gly Asn Ser Thr Arg Ser Pro Glu Thr Asn Gly Leu Leu Cys Gly
 1               5                  10                  15

Asp Pro Glu Glu Asn Cys Ala Ala Thr Thr Thr Gln Ser Lys Arg Lys
            20                  25                  30

Gly His Phe Ser Arg Cys Pro Lys
        35                  40

<210> SEQ ID NO 58
<211> LENGTH: 36
<212> TYPE: PRT
<213> ORGANISM: Human

<400> SEQUENCE: 58
```

-continued

```
Gln Tyr Lys His Tyr Cys Ile Lys Gly Arg Cys Arg Phe Val Val Ala
  1               5                  10                  15

Glu Gln Thr Pro Ser Cys Val Cys Asp Glu Gly Tyr Ile Gly Ala Arg
             20                  25                  30

Cys Glu Arg Val
         35

<210> SEQ ID NO 59
<211> LENGTH: 37
<212> TYPE: PRT
<213> ORGANISM: Human

<400> SEQUENCE: 59

Asp Gly Asn Ser Thr Arg Ser Pro Glu Thr Asn Gly Leu Leu Cys Gly
  1               5                  10                  15

Asp Pro Glu Glu Asn Cys Ala Ala Thr Thr Thr Gln Ser Lys Arg Lys
             20                  25                  30

Gly His Phe Ser Arg
         35

<210> SEQ ID NO 60
<211> LENGTH: 39
<212> TYPE: PRT
<213> ORGANISM: Human

<400> SEQUENCE: 60

Cys Pro Lys Gln Tyr Lys His Tyr Cys Ile Lys Gly Arg Cys Arg Phe
  1               5                  10                  15

Val Val Ala Glu Gln Thr Pro Ser Cys Val Cys Asp Glu Gly Tyr Ile
             20                  25                  30

Gly Ala Arg Cys Glu Arg Val
         35

<210> SEQ ID NO 61
<211> LENGTH: 75
<212> TYPE: PRT
<213> ORGANISM: Human

<400> SEQUENCE: 61

Gly Asn Ser Thr Arg Ser Pro Glu Thr Asn Gly Leu Leu Cys Gly Asp
  1               5                  10                  15

Pro Glu Glu Asn Cys Ala Ala Thr Thr Thr Gln Ser Lys Arg Lys Gly
             20                  25                  30

His Phe Ser Arg Cys Pro Lys Gln Tyr Lys His Tyr Cys Ile Lys Gly
         35                  40                  45

Arg Cys Arg Phe Val Val Ala Glu Gln Thr Pro Ser Cys Val Cys Asp
     50                  55                  60

Glu Gly Tyr Ile Gly Ala Arg Cys Glu Arg Val
 65                  70                  75

<210> SEQ ID NO 62
<211> LENGTH: 23
<212> TYPE: PRT
<213> ORGANISM: Human

<400> SEQUENCE: 62

Asp Gly Asn Ser Thr Arg Ser Pro Glu Thr Asn Gly Leu Leu Cys Gly
  1               5                  10                  15

Asp Pro Glu Glu Asn Cys Ala
```

```
<210> SEQ ID NO 63
<211> LENGTH: 53
<212> TYPE: PRT
<213> ORGANISM: Human

<400> SEQUENCE: 63

Ala Thr Thr Thr Gln Ser Lys Arg Lys Gly His Phe Ser Arg Cys Pro
 1               5                  10                  15
Lys Gln Tyr Lys His Tyr Cys Ile Lys Gly Arg Cys Arg Phe Val Val
                20                  25                  30
Ala Glu Gln Thr Pro Ser Cys Val Cys Asp Glu Gly Tyr Ile Gly Ala
                    35                  40                  45
Arg Cys Glu Arg Val
        50

<210> SEQ ID NO 64
<211> LENGTH: 30
<212> TYPE: PRT
<213> ORGANISM: Human

<400> SEQUENCE: 64

Asp Gly Asn Ser Thr Arg Ser Pro Glu Thr Asn Gly Leu Leu Cys Gly
 1               5                  10                  15
Asp Pro Glu Glu Asn Cys Ala Ala Thr Thr Thr Gln Ser Lys
                20                  25                  30
```

BETACELLULIN MODIFICATION

TECHNICAL FIELD

The present invention relates to muteins (hereinafter, sometimes to be referred to as mutated molecules) with less epithelial cell growth promoting activity (EGF activity) such as for smooth muscle cells while preserving activity in differentiating betacellulin (BTC) into pancreatic β cells (BTC activity), as well as a manufacturing method thereof, etc.

BACKGROUND ART

Human betacellulin is a protein factor consisting of 80 amino acids excised from a precursor consisting of 178 amino acids. The entire amino acid sequence has been identified (Sasada et al, *Biochem. Biophys. Res. Commun.*, 190:1173 (1993)). Endogenous betacellulin occurs in extremely minute amounts, and it is difficult to obtain the endogenous betacellulin. However, a method for manufacture using a recombinant technique has been disclosed in Japanese Unexamined Patent Application (Kokai) H6-87894, etc. Betacellulin was first discovered as a factor having mouse 3T3 cell growth promoting activity, and has subsequently been found to have vascular smooth muscle cell and retinal pigment epithelial cell growth promoting activity (EGF activity) (Shing et al, *Science*, 259:1604 (1993)). Betacellulin also acts on pancreatic undifferentiated cells, promoting their differentiation to pancreatic β cells which produce insulin (BTC activity) (Mashima et al, *J. Clinic. Invest.*, 97:1647 (1996)), and is thus considered to be a potentially useful as prophylactic and therapeutic agent for diabetes (such as insulin-dependent diabetes) as well as pancreatic dysfunction and the like associated with diabetes (Miyagawa et al, Abstracts of the 1997 Japan Diabetes Association Conference, 125).

However, since betacellulin has such vascular smooth muscle cell and retinal pigment epithelial cell growth promoting activity, these activities have proven to be a problem in applications as a therapeutic agent for diabetes.

The potential of such pharmaceuticals could therefore be improved if the growth promoting activity of the vascular smooth muscle cells and the like could be reduced while preserving the action in promoting pancreatic β cell differentiation, but no such betacellulin muteins are thus far known.

DISCLOSURE OF THE INVENTION

As a result of extensive research on betacellulin muteins, the inventors perfected the present invention upon the discovery and further research of muteins in which betacellulin mutations allowed the smooth vascular muscle growth promoting activity and the like to be reduced while preserving the pancreatic β cell differentiation promoting activity, with no antigenicity-related problems when administered to the living body. That is, the present invention relates to betacellulin muteins, a method for obtaining said muteins and the like That is, the present invention relates to:

1. A betacellulin mutein or a salt thereof, wherein the pancreatic β cell differentiation promoting activity is preserved, and the epithelial cell growth promoting activity is reduced.

2. A betacellulin mutein or salt thereof according to 1 above, wherein the ratio of the pancreatic β cell differentiation promoting activity to the epithelial cell growth promoting activity is at least twice relative to that of betacellulin.

3. A betacellulin mutein or salt thereof according to 1 above, wherein 1 to 40 amino acid residues from the N terminal of the betacellulin may be deleted, and 1 to 4 of the first through fourth amino acid residues from the C terminal, including the Leu at 3 from the C terminal and the Asp at 4 from the C terminal, may be deleted or substituted with other amino acid residues or other peptide chains.

4. A betacellulin mutein or salt thereof according to 3 above, wherein 1 to 40 amino acid residues from the N terminal have been deleted.

5. A betacellulin mutein or salt thereof according to 3 above, comprising 1) an amino acid sequence represented by SEQ ID NO: 1, 2) an amino acid sequence in which 1 to 40 amino acids from the N terminal in the amino acid sequence represented by SEQ ID NO: 1 have been deleted, 3) an amino acid sequence represented by SEQ ID NO: 2, or 4) an amino acid sequence in which 1 to 40 amino acids from the N terminal in the amino acid sequence represented by SEQ ID NO: 2 have been deleted.

6. A betacellulin or salt thereof according to 3 above, comprising 1) an amino acid sequence represented by SEQ ID NO: 1, 2) an amino acid sequence represented by SEQ ID NO: 2, 3) an amino acid sequence represented by SEQ ID NO: 3, or 4) an amino acid sequence represented by SEQ ID NO: 4.

7. A betacellulin or salt thereof according to 3 above, comprising 1) an amino acid sequence represented by SEQ ID NO: 37, or 2) an amino acid sequence represented by SEQ ID NO: 38.

8. A betacellulin or salt thereof according to 1 above, wherein 1 to 30 amino acid residues from the N terminal of the betacellulin may be deleted, and 1 to 5 amino acid residues may be inserted between the $22^{nd}$ and $23^{rd}$ amino acid residues from the C terminal.

9. A betacellulin or salt thereof according to 8 above, wherein 1 to 30 amino acid residues from the N terminal of the betacellulin have been deleted.

10. A betacellulin or salt thereof according to 8 above, comprising the amino acid sequence represented by SEQ ID NO: 44.

11. A betacellulin or salt thereof according to 8 above, comprising the amino acid sequence represented by SEQ ID NO: 45.

12. A method for manufacturing a betacellulin or salt thereof according to 1 above, characterized by culturing the transformants which have been transformed with recombinant vectors containing DNA encoding the betacellulin according to 1 above to produce said betacellulin mutein.

13. A pharmaceutical composition comprising a betacellulin or salt thereof according to 1 above.

14. A pharmaceutical composition according to 9 above, wherein the composition is a prophylactic or therapeutic drug for diabetes.

15. A prophylactic or therapeutic method for diabetes, characterized in that a betacellulin or salt thereof according to 1 above is administered to mammals.

16. The use of a betacellulin or salt thereof according to 1 above to manufacture a prophylactic or therapeutic agent for diabetes.

BEST MODE FOR CARRYING OUT THE INVENTION

Figure 1:
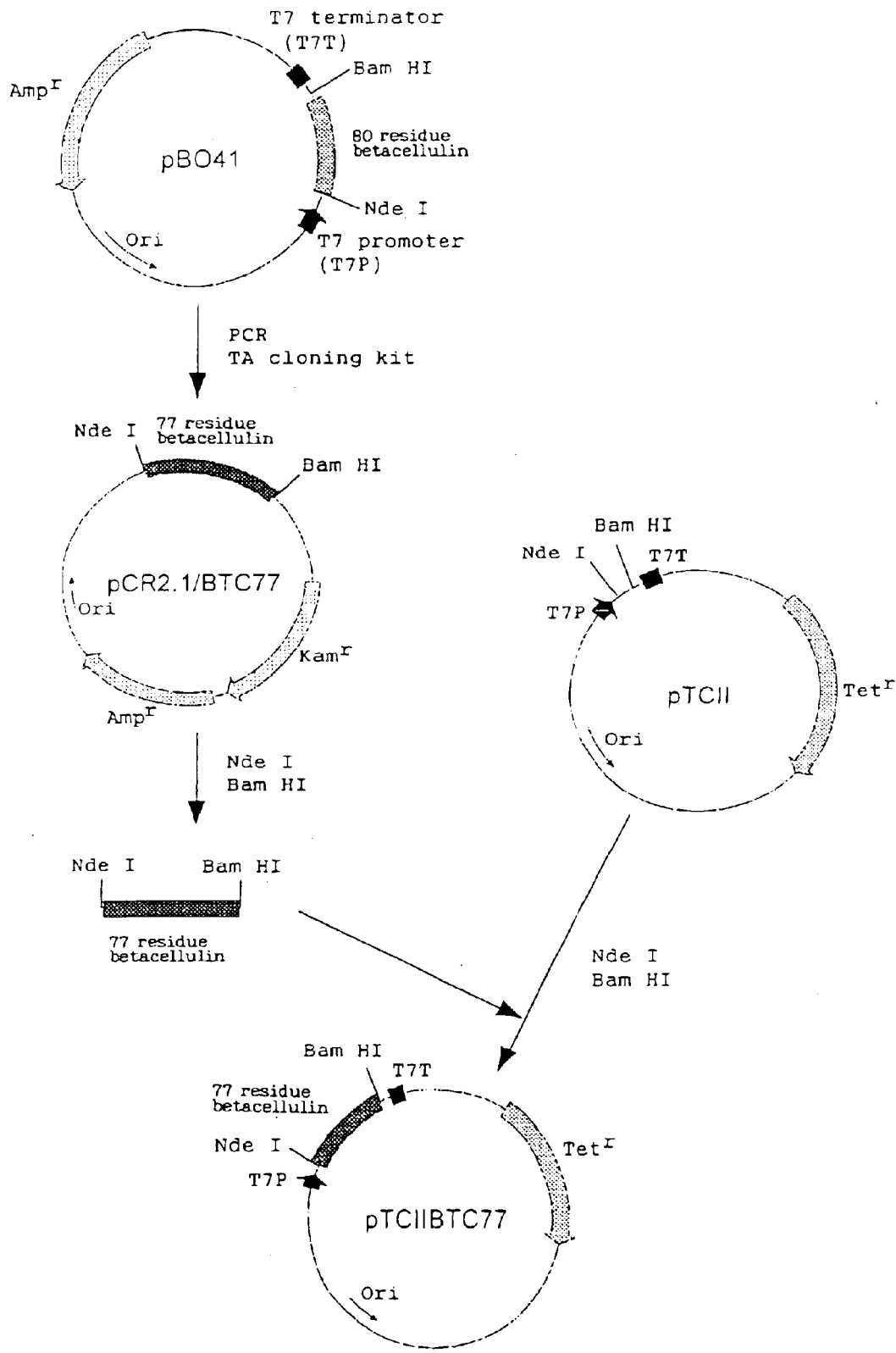
FIG. 1 illustrates the construction of an expression plasmid for 77 residue betacellulin (with three C terminal residues deleted)

As described above, the betacellulin muteins of the present invention have reduced or attenuated EGF activity while preserving intact BTC activity.

As used herein, betacellulin means a polypeptide having the amino acid sequence represented by the following, SEQ ID NO: 35, as described in Sasada et al., *Biochem. Biophys. Res. Commun.*, 190:1173 (1993)).

Asp Gly Asn Ser Thr Arg Ser Pro Glu Thr Asn Gly Leu
Leu Cys Gly Asp Pro Glu Glu Asn Cys Ala Ala Thr Thr
Thr Gln Ser Lys Arg Lys Gly His Phe Ser Arg Cys Pro
Lys Gln Tyr Lys His Tyr Cys Ile Lys Gly Arg Cys Arg
Phe Val Val Ala Glu Gln Thr Pro Ser Cys Val Cys Asp
Glu Gly Tyr Ile Gly Ala Arg Cys Glu Arg Val Asp Leu
Phe Tyr

Betacellulin muteins with intact BTC activity are those having at least 20%, and preferably at least 50%, of the BTC activity of betacellulin.

Betacellulin muteins with reduced EGF activity are those having less than or equal to 20%, and preferably less than or equal to 15%, of the EGF activity of betacellulin.

Examples of betacellulin muteins with deduced EGF activity and intact BTC activity of the present invention preferably include betacellulin muteins, or their salts, in which the ratio of the pancreatic β cell differentiation promoting activity to the epithelial cell growth promoting activity is at least twice relative to that of betacellulin.

Specific examples of betacellulin muteins with reduced EGF activity and intact BTC activity of the present invention include betacellulin muteins, or their salts, in which 1 to 40 amino acid residues may be deleted from the N terminal of the betacellulin, and 1 to 4 amino acid residues of the first through fourth amino acid residues from the C terminal, including the Leu at 3 from the C terminal and the Asp at 4 from the C terminal, may be deleted or substituted with other amino acid residues or other peptide chains. More specific examples include the aforementioned betacellulin muteins or the like in which 1 to 40 or 1 to 20 amino acid residues have been deleted from the N terminal.

The aforementioned "substitution by other amino acid residues or other peptide chains" mentioned in the expression "betacellulin muteins in which residues are substituted with other amino acid residues or other peptide chains" may refer to any type of amino acid residue or peptide chain, provided that the substitution does not compromise the characteristic feature of the betacellulin mutein which results in "reduced EGF activity and intact BTC activity." Specific examples of "other amino acids" above include nonpolar (hydrophobic) amino acids (such as alanine, leucine, isoleucine, valine, proline, phenylalanine, tryptophan, and methionine), polar (neutral) amino acids (such as glycine, serine, threonine, cysteine, tyrosine, asparagine, and glutamine), amino acids with a positive charge (basic) (such as arginine, lysine, and histidine), and amino acids with a negative charge (acidic) (such as aspartic acid and glutamic acid). Specific examples of the "other peptide chains" above refer to peptide chains of two or more "other amino acids" bound together, and preferably includes peptide chains consisting of 2 to 4 amino acid residues.

The following are specific examples of "betacellulin muteins in which 1 to 40 amino acid residues may be deleted from the N terminal of the betacellulin, and 1 to 4 amino acid residues of the first through fourth amino acid residues from the C terminal, including the Leu at 3 from the C terminal and the Asp at 4 from the C terminal, may be deleted or substituted with other amino acid residues or other peptide chains."

(1) Betacellulin muteins having the following amino acid sequence up to the 76th position from the N terminal of betacellulin, Asp Gly Asn Ser Thr Arg Ser Pro Glu Thr Asn Gly Leu
Leu Cys Gly Asp Pro Glu Glu Asn Cys Ala Ala Thr Thr Thr
Gln Ser Lys Arg Lys Gly His Phe Ser Arg Cys Pro Lys Gln
Tyr Lys His Tyr Cys Ile Lys Gly Arg Cys Arg Phe Val Val
Ala Glu Gln Thr Pro Ser Cys Val Cys Asp Glu Gly Tyr Ile
Gly Ala Arg Cys Glu Arg Val (SEQ ID NO:2).

where 1 to 4 amino acid residues of the first through fourth amino acid residues (Asp Leu Phe Tyr) from the C terminal, including the Leu at 3 from the C terminal and the Asp at 4 from the C terminal, has been deleted or substituted with other amino acid residues or other peptide chains such as ((1)) betacellulin muteins having the amino acid sequence represented by SEQ ID NO: 2:
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val.

((2)) betacellulin muteins having the amino acid sequence represented by SEQ ID NO: 1:
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val Asp ((3)) betacellulin muteins having the amino acid sequence represented by SEQ ID NO: 5:
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val Leu Phe Tyr ((4)) betacellulin muteins having the amino acid sequence represented by SEQ ID NO: 6:
Asp Gly Asn Ser Thr Arg Ser Pro Glu Thr Asn Gly Leu Leu
Cys Gly Asp Pro Glu Glu Asn Cys Ala Ala Thr Thr Thr Gln Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val Leu Phe
((5)) betacellulin muteins having the amino acid sequence represented by SEQ ID NO: 7:
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val Leu
((6)) betacellulin muteins having the amino acid sequence represented by SEQ ID NO: 8:
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val Asp Phe Tyr
((7)) betacellulin muteins having the amino acid sequence represented by SEQ ID NO: 9:
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Thr Pro Ser Cys Val Cys Asp Glu Gly Tyr Ile Gly
Ala Arg Cys Glu Arg Val Asp Phe
((8)) betacellulin muteins in which the amino acid residue at 3 (Leu) from the C terminal of betacellulin is substituted with another amino acid residue.

Of the above, betacellulin muteins with the amino acid sequences represented by SEQ ID NOs: 1 and 2 are particularly preferred.

(2) Betacellulin proteins in which the $1^{st}$ to $40^{th}$ amino acid residues may be deleted from the N terminal of betacellulin
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys (SEQ ID NO: 57) the mutein has the following amino acid sequence from the $41^{st}$ through $76^{th}$ residues from the N terminal
Gln Tyr Lys His Tyr Cys Ile Lys Gly Arg Cys Arg Phe Val
Val Ala Glu Gln Thr Pro Ser Cys Val Cys Asp Glu Gly Tyr
Ile Gly Ala Arg Cys Glu Arg Val (SEQ ID NO: 58)
and 1 to 4 amino acid residues of the first through fourth amino acid residues (Asp Leu Phe Tyr) from the C terminal, including the Leu at 3 from the C terminal and the Asp at 4 from the C terminal, are deleted or substituted with other amino acid residues or other peptide chains, preferably
(i) betacellulin muteins in which the $1^{st}$ to $37^{th}$ amino acid residues from the N terminal of betacellulin may be deleted
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg (SEQ ID NO: 59)
the mutein has the following amino acid sequence from the $38^{th}$ through $76^{th}$ residues from the N terminal
Cys Pro Lys Gln Tyr Lys His Tyr Cys Ile Lys Gly Arg Cys
Arg Phe Val Val Ala Glu Gln Thr Pro Ser Cys Val Cys Asp
Glu Gly Tyr Ile Gly Ala Arg Cys Glu Arg Val (SEQ ID NO: 60)
and 1 to 4 amino acid residues of the first through fourth amino acid residues (Asp Leu Phe Tyr) from the C terminal, including the Leu at 3 from the C terminal and the Asp at 4 from the C terminal, are deleted or substituted with other amino acid residues or other peptide chains
(ii) betacellulin muteins in which the $1^{st}$ amino acid residue (Asp) from the N terminal of betacellulin may be deleted,
the mutein has the following amino acid sequence from the $2^{nd}$ through $76^{th}$ residues from the N terminal
Gly Asn Ser Thr Arg Ser Pro Glu Thr Asn Gly Leu Leu Cys
Gly Asp Pro Glu Glu Asn Cys Ala Ala Thr Thr Thr Gln Ser
Lys Arg Lys Gly His Phe Ser Arg Cys Pro Lys Gln Tyr Lys
His Tyr Cys Ile Lys Gly Arg Cys Arg Phe Val Val Ala Glu
Gln Thr Pro Ser Cys Val Cys Asp Glu Gly Tyr Ile Gly Ala
Arg Cys Glu Arg Val (SEQ ID NO: 6 1)
and 1 to 4 amino acid residues of the first through fourth amino acid residues (Asp Leu Phe Tyr) from the C terminal, including the Leu at 3 from the C terminal and the Asp at 4 from the C terminal, are deleted or substituted with other amino acid residues or other peptide chains
(iii) betacellulin muteins in which the $1^{st}$ through $23^{rd}$ amino acid residues from the N terminal of betacellulin may be deleted
Asp Gly Asn Ser Thr Arg Ser Pro Glu Thr Asn Gly Leu Leu
Cys Gly Asp Pro Glu Glu Asn Cys Ala (SEQ ID NO: 62)
the mutein has the following amino acid sequence from the $24^{th}$ through $76^{th}$ residues from the N terminal
Ala Thr Thr Thr Gln Ser Lys Arg Lys Gly His Phe Ser Arg
Cys Pro Lys Gln Tyr Lys His Tyr Cys Ile Lys Gly Arg Cys
Arg Phe Val Val Ala Glu Gln Thr Pro Ser Cys Val Cys Asp
Glu Gly Tyr Ile Gly Ala Arg Cys Glu Arg Val (SEQ ID NO: 63)
and 1 to 4 amino acid residues of the first through fourth amino acid residues (Asp Leu Phe Tyr) from the C terminal, including the Leu at 3 from the C terminal and the Asp at 4 from the C terminal, are deleted or substituted with other amino acid residues or other peptide chains, preferably
((1)) betacellulin muteins having the amino acid sequence represented by SEQ ID NO: 4:
Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val
((2)) betacellulin muteins having the amino acid sequence represented by SEQ ID NO: 3:
Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val Asp
((3)) betacellulin muteins having the amino acid sequence represented by SEQ ID NO: 10:
Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val Leu Phe Tyr
((4)) betacellulin muteins having the amino acid sequence represented by SEQ ID NO: 11:
Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val Leu Phe
((5)) betacellulin muteins having the amino acid sequence represented by SEQ ID NO: 12:
Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val Leu
((6)) betacellulin muteins having the amino acid sequence represented by SEQ ID NO: 13:
Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val Asp Phe Tyr
((7)) betacellulin muteins having the amino acid sequence represented by SEQ ID NO: 14:

Arg Lys Gly His Phe Ser Arg Cys Pro Lys Gln Tyr Lys His
Tyr Cys Ile Lys Gly Arg Cys Arg Phe Val Val Ala Glu Gln
Thr Pro Ser Cys Val Cys Asp Glu Gly Tyr Ile Gly Ala Arg
Cys Glu Arg Val Asp Phe
((8)) betacellulin muteins in which the $3^{rd}$ amino acid residue from the C terminal (Leu) in partial peptides represented by the amino acid sequence from 31 through 80 of the N terminal of betacellulin is substituted with another amino acid residue
((9)) betacellulin muteins having the amino acid sequence represented by SEQ ID NO: 37:
Gly Asn Ser Thr Arg Ser Pto Glu Thr Asn Gly Leu Leu Cys
Gly Asp Pro Glu Glu Asn Cys Ala Ala Thr Thr Thr Gln Ser
Lys Arg Lys Gly His Phe Ser Arg Cys Pro Lys Gln Tyr Lys
His Tyr Cys Ile Lys Gly Arg Cys Arg Phe Val Val Ala Glu
Gln Thr Pro Ser Cys Val Cys Asp Glu Gly Tyr Ile Gly Ala
Arg Cys Glu Arg Val
((10)) betacellulin muteins having the amino acid sequence represented by SEQ ID NO: 38:
Ala Thr Thr Thr Gln Ser Lys Arg Lys Gly His Phe Ser Arg
Cys Pro Lys Gln Tyr Lys His Tyr Cys Ile Lys Gly Arg Cys
Arg Phe Val Val Ala Glu Gln Thr Pro Ser Cys Val Cys Asp
Glu Gly Tyr Ile Gly Ala Arg Cys Glu Arg Val Preferred among these are betacellulin muteins with amino acid sequences represented by SEQ ID NOs: 3, 4, 37, and 38. Betacellulin muteins with amino acid sequences represented by SEQ ID NOs: 37 and 38 are more preferable. Betacellulin muteins with the amino acid sequence represented by SEQ ID NO: 38 are most preferable.

Among the preferred examples of betacellulin muteins of the present invention given in (1) and (2) above, especially preferable examples include betacellulin muteins with ((1)) an amino acid sequence represented by SEQ ID NO: 1, ((2)) an amino acid sequence in which 1 through 40 amino acids from the N terminal have been deleted in the amino acid sequence represented by SEQ ID NO: 1, ((3)) an amino acid sequence represented by SEQ ID NO: 2, ((4)) an amino acid sequence in which 1 through 40 amino acids from the N terminal have been deleted in the amino acid sequence represented by SEQ ID NO: 2, ((5)) an amino acid sequence represented by SEQ ID NO: 37, and ((6)) an amino acid sequence represented by SEQ ID NO: 38.

Especially preferable are betacellulin muteins with ((1)) an amino acid sequence represented by SEQ ID NO: 1, ((2)) an amino acid sequence represented by SEQ ID NO: 2, ((3)) an amino acid sequence represented by SEQ ID NO: 3, ((4)) an amino acid sequence represented by SEQ ID NO: 4, ((5)) an amino acid sequence represented by SEQ ID NO: 37, and ((6)) an amino acid sequence represented by SEQ ID NO: 38. Particularly preferable are betacellulin muteins with the amino acid sequence represented by SEQ ID NO: 38.

Specific examples of betacellulin muteins of the present invention which have reduced EGF activity and intact BTC activity include (1) betacellulin muteins or salts thereof in which 1 to 30 amino acid residues of the N terminal of betacellulin may be deleted, and 1 to 5 amino acid residues have been inserted between the $22^{nd}$ and $23^{rd}$ amino acid residues from the C terminal, and (2) betacellulin muteins or salts thereof with an aqueous solution represented by SEQ ID NO: 45.

Specific examples of "amino acids" in "betacellulin muteins in which such amino acid residues have been inserted" include nonpolar (hydrophobic) amino acids (such as alanine, leucine, isoleucine, valine, proline, phenylalanine, tryptophan, and methionine), polar (neutral) amino acids (such as glycine, serine, threonine, cysteine, tyrosine, asparagine, and glutamine), amino acids with a positive charge (basic) (such as arginine, lysine, and histidine), and amino acids with a negative charge (acidic) (such as aspartic acid and glutamic acid). Asparagine, proline, and serine are preferred. Specific examples of "peptide chains" above refer to peptide chains of two to five such "amino acids" bound together, and preferably includes peptide chains consisting of 2 to 4 amino acid residues.

Examples of "betacellulin in which 1 to 30 amino acid residues of the N terminal may be deleted" include (1) polypeptides with an amino acid sequence represented by the aforementioned SEQ ID NO: 35, (2) betacellulin muteins in which 1 to 30 amino acid residues of the N terminal have been deleted, and (3) betacellulin muteins in which amino acid residues (e.g., 1 to 5 amino acid residues) have been inserted in the amino acid sequence of the $1^{st}$ through $30^{th}$ residues of the N terminal of betacellulin.

"Betacellulin muteins in which 1 to 30 amino acid residues of the N terminal have been deleted" include 1) those in which 1 to 30 amino acid residues of the N terminal of betacellulin have been deleted, and 2) those in which 1 to 30 amino acid residues of the N terminal of betacellulin have been deleted, and other amino acid residues (e.g., 1 to 5 amino acid residues) have been added.

"Betacellulin muteins in which 1 to 30 amino acid residues of the N terminal may be deleted, and 1 to 5 amino acid residues have been inserted between the $22^{nd}$ amino acid residue of the C terminal (i.e., Gln, the $58^{th}$ amino acid residue from the N terminal in the amino acid sequence represented by SEQ ID NO: 35) and the $23^{rd}$ amino acid residue (i.e., Thr, the $59^{th}$ amino acid residue from the N terminal in the amino acid sequence represented by SEQ ID NO: 35)" should be betacellulin muteins in which some of 1 through 30 amino acid residues of the N terminal of betacellulin may be deleted, and 1 to 5 amino acid residues have been inserted between the $22^{nd}$ and $23^{rd}$ amino acid residues from the C terminal. Specific examples include:
((1)) betacellulin muteins with an amino acid sequence represented by SEQ ID NO: 46
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys Arg Lys Gly His Phe Ser Arg Cys Pro Lys Gln Tyr
Lys His Tyr Cys Ile Lys Gly Arg Cys Arg Phe Val Val Ala
Glu Gln Asn Pro Ser Thr Pro Ser Cys Val Cys Asp Glu Gly
Tyr Ile Gly Ala Arg Cys Glu Arg Val Asp Leu Phe Tyr
((2)) betacellulin muteins in which the $1^{st}$ through $30^{th}$ amino acid residues from the N terminal of betacellulin have been deleted
Asp Gly Asn Ser Thr Arg Ser Pro Glu Thr Asn Gly Leu Leu
Cys Gly Asp Pro Glu Glu Asn Cys Ala Ala Thr Thr Thr Gln
Ser Lys (SEQ ID NO: 64)
and 1 to 5 amino acid residues have been inserted between the $22^{nd}$ and $23^{rd}$ amino acid residues from the C terminal, such as a betacellulin mutein with an amino acid sequence represented by SEQ ID NO: 44:
Arg Lys Gly His Phe Ser Arg Cys Pro Lys Gln Tyr Lys His
Tyr Cys Ile Lys Gly Arg Cys Arg Phe Val Val Ala Glu Gln
Asn Pro Ser Thr Pro Ser Cys Val Cys Asp Glu Gly Tyr Ile
Gly Ala Arg Cys Glu Arg Val Asp Leu Phe Tyr Preferred examples of "betacellulin muteins" of the present invention include the betacellulin muteins having an amino acid sequence represented by SEQ ID NO: 44 or 45.

In accordance with the conventional manner for designating peptides, the left terminal of the betacellulin muteins in the present Specification is referred to as the N terminal (amino terminal), and the right terminal is referred to as the C terminal (carboxyl terminal). The C terminal of these betacellulin muteins is usually a carboxyl group (—COOH)

or carboxylate (—COO⁺), but the C terminal may also be an amide (—CONH₂) or ester (—COOR). Examples of R in such esters include $C_{1-6}$ alkyl groups such as methyl, ethyl, n-propyl, isopropyl, or n-butyl, $C_{3-8}$ cycloalkyl groups such as cyclopentyl and cyclohexyl, $C_{6-12}$ aryl groups such as phenyl and α-naphthyl, phenyl-$C_{1-2}$ alkyls such as benzyl, phenethyl, and benzhydryl, or $C_{7-14}$ aralkyl groups such as α-naphthyl-$C_{1-2}$ alkyls such as α-naphthylmethyl, and pivaloyloxymethyl groups.

The betacellulin muteins of the present invention include those with Met added to the N terminal.

Examples of salts of the betacellulin muteins of the present invention include salts with physiologically acceptable bases (e.g., alkali metals) or acids (organic and inorganic acids), in particular physiologically acceptable acid salts are preferred. Examples of such salts include salts with inorganic acids (e.g., hydrochloric acid, phosphoric acid, hydrobromic acid, and sulfuric acid), and acids with organic acids (e.g., acetic acid, formic acid, propionic acid, fumaric acid, maleic acid, succinic acid, tartaric acid, citric acid, malic acid, oxalic acid, benzoic acid, methanesulfonic acid, and benzenesulfonic acid).

The betacellulin muteins of the present invention can be prepared by genetic engineering as described in Japanese Unexamined Patent Application (Kokai) H6-87894, for example, or by a protease treatment that is publicly known, preferably a carboxypeptidase treatment, and even more preferably bovine pancreatic carboxypeptidase A treatment, of betacellulin obtained by the culture of beta tumor cells. They can also be prepared according to the peptide synthesis described below. They can furthermore be manufactured by the culture of transformants containing DNA encoding betacellulin muteins, as described below.

When the betacellulin is manufactured from human or mammalian tissue or cells, the human or mammalian tissue or cells should be homogenized and then extracted with acid or the like, and the extract should be purified and isolated through a combination of salting out, dialysis, gel filtration, and chromatography such as reverse phase chromatography, ion exchange chromatography, and affinity chromatography.

Peptides may be synthesized by either solid phase synthesis or liquid phase synthesis, for example. That is, partial peptides or amino acids capable of composing the betacellulin muteins of the present invention are condensed with the remainder, and protection groups are eliminated when the product has protection groups, whereby the target betacellulin muteincan be manufactured. The publicly known methods for condensation and the removal of protection groups include the following methods in (1) through (5).

(1) M. Bodanszky and M. A. Ondetti, *Peptide Synthesis*, Interscience Publishers, New York (1966)

(2) Schroeder and Luebke, *The Peptide, Academic* Press, New York (1965)

(3) Nobuo Izumiya et al, *Peptide Synthesis Fundamentals and Experiments*, Maruzen (1975)

(4) Jimei Yashima and Toshihira Kashiwahara, *Basic Biochemical Experiments*, Vol. 1, Protein Chemistry IV, 205 (1977)

(5) Sequel Development of Medical Drugs, Vol. 14, *Peptide Synthesis*, Kadokawa Shoten, Ed. Jimei Yashima After the reaction, the polypeptide of the present invention can be purified and isolated by a combination with, for example, solvent extraction, distillation, column chromatography, liquid chromatography, and recrystallization. When the resulting polypeptide is in free form, it can be converted to a suitable salt by a publicly known method. Alternatively, when a salt form is obtained, it can be converted to free form by a publicly known method.

Commercially available peptide binding resins suitable for amide formation can be used for amide forms of betacellulin. Examples of such resins include chloromethyl resins, hydroxymethyl resins, benzhydrylamine resins, aminomethyl resins, 4-benzyloxybenzyl alcohol resins, 4-methylbenzhydrylamine resins, PAM resins, 4-hydroxymethyl methylphenyl acetamide methyl resins, polyacrylamide resins, 4-(2',4'-dimethoxyphenylhydroxymethyl)phenoxy resins, and 4-(2',4'-dimethoxyphenyl-Fmoc aminoethyl)phenoxy resins. Such resins can be used for the condensation of amino acids with suitably protected side chain functional groups and α-amino groups on resin in accordance with various publicly known methods of condensation as befits the sequence of the intended peptide. After the reaction, the peptide is excised from the resin, the various protection groups are simultaneously removed, and a reaction for forming-intramolecular disulfide bonds is brought about in a highly diluted solution as needed to obtain the target amide forms.

Although various activating reagents that can be used for peptide synthesis may be used for the condensation of such protected amino acids, carbodiimides are particularly preferred. Examples of carbodiimides include DCC, N,N'-diisopropylcarbodiimide, and N-ethyl-N'-(3-dimethylaminopropyl)carbodiimide. For activation with the above, racemization inhibitors (e.g., HOBt and HOOBt) and protected amino acids can be added directly to the resin, or they can be added in the form of corresponding acid anhydrides or HOBt esters or HOOBt esters to the resin after the activation of the protected amino acids. Solvents which are used for the condensation with resins or the activation of protected amino acids can be suitably selected from solvents which are known to be capable of being used for peptide condensation. Examples include acid amides such as N,N-dimethylformamide, N,N-dimethylacetamide, and N-methylpyrrolidone, halogenated hydrocarbons such as methylene chloride and chloroform, alcohols such as trifluoroethanol, sulfoxides such as dimethylsulfoxide, tertiary amines such as pyridine, ethers such as dioxane and tetrahydrofuran, nitriles such as acetonitrile and propionitrile, esters such as methyl acetate and ethyl acetate, and suitable mixtures of the above. The reaction temperature can be suitably selected from within the known usable range in the formation of peptide bonds, which is usually about −20 to 50° C. Activated amino acid derivatives are usually used in an excess amount of 1.5 to 4 folds. When ninhydrin reaction tests reveal insufficient condensation, the condensation is repeated without removing the protection groups until sufficient condensation has been achieved. When repeated reaction fails to provide sufficient condensation, acetic acid anhydride or acetyl imidazole may be used for the acetylation of the unreacted amino acids to avoid influencing subsequent reactions.

Examples of protection groups for the amino groups of starting material amino acids include Z, Boc, tertiary-pentyloxycarbonyl, isobornyloxycarbonyl, 4-methoxybenzyloxycarbonyl, Cl—Z, Br—Z, adamantyloxycarbonyl, trifluoroacetyl, phthaloyl, formyl, 2-nitrophenylsulfenyl, diphenylphosphinothioyl, and Fmoc. Examples of protection groups for carboxyl groups include those in which R is a $C_{1-6}$ alkyl group, $C_{3-8}$ cycloalkyl group, or $C_{7-14}$ aralkyl group, as well as 2-adamantyl, 4-nitrobenzyl, 4-methoxybenzyl, and 4-chlorobenzyl, phenacyl groups, and benzyloxycarbonylhydrazide, tertiary-butoxycarbonylhydrazide, and tritylhydrazide.

The hydroxyl groups of serine and threonine can be protected, for example, by esterification or etherification.

Examples of groups that are suitable for esterification include lower alkanoyl groups such as acetyl, alloyl groups such as benzoyl, and carbon-derived groups such as benzyloxycarbonyl and ethoxycarbonyl. Examples of groups that are suitable for etherification include benzyl, tetrahydropyranyl, and tertiary-butyl groups.

Examples of protection groups for phenolic hydroxyl groups of tyrosine include Bzl, $Cl_2$—Bzl, 2-nitrobenzyl, Br—Z, and tertiary-butyl.

Examples of protection groups for imidazoles of histidine include Tos, 4-methoxy-2,3,6-trimethylbenzenesulfonyl, DNP, benzyloxymethyl, Bum, Boc, Trt, and Fmoc.

Examples for activated carboxyl groups in the starting material include corresponding acid anhydrides, azides, and active esters (esters with alcohols (e.g., pentachlorophenol, 2,4,5-trichlorophenol, 2,4-dinitrophenol, cyanomethyl alcohol, para-nitrophenol, HONB, N-hydroxysuccimide, N-hydroxyphthalimide, and HOBt)). Examples for activated amino groups in the starting material include the corresponding phosphoric amides.

Methods for removing (eliminating) protection groups include direct contact reduction in a hydrogen flow in the presence of a catalyst such as Pd black or Pd carbon, acid treatment with anhydrous hydrogen fluoride, methanesulfonic acid, trifluoromethanesulfonic acid, trifluoroacetic acid, or mixtures thereof, base treatment with diisopropylethylamine, triethylamine, piperidine, or piperazine, or reduction with sodium in liquid ammonia. The eliminating reaction by acid treatment above performed at a temperature of −20 to 40° C., but it is effective to add a cation scavenger such as anisol, phenol, thioanisol, meta-cresol, para-cresol, dimethylsulfide, 1,4-butanedithiol, or 1,2-ethanedithiol. 2,4-dinitrophenyl used as a imidazole protection group for histidine can be removed by treatment with thiophenol, while formyl groups used as indole protection groups for tryptophan can be removed by acid treatment in the presence of the aforementioned 1,2-ethanediol, 1,4-butanedithiol, or the like, and can also be removed by alkali treatment with diluted sodium hydroxide, diluted ammonia, or the like.

Methods for introducing protection groups to functional groups which are not to be involved in the reaction, the elimination of such protection groups, the activation of functional groups involved in the reaction, and the like should be managed by publicly know methods or modification thereof.

In another method for obtaining an amide form of betacellulin muteins, the α-carboxyl group of the carboxyl terminal amino acid is first amidated, the peptide chain is then extended to the desired length to the amino group side, a peptide except for only the protection groups for the α-amino groups on the N terminal of the peptide chain and a peptide (or amino acid) except for only the protection groups for the carboxyl groups on the C terminal are then prepared, and the two peptides are allowed to undergo condensation in a solvent mixture such as the above. The details of the condensation are the same as above. After the protected peptides resulting from the condensation have been purified, all the protection groups can removed by the methods described above to obtain the desired crude polypeptide. The crude polypeptide can be purified through a variety of known purification techniques, and the main fractions can be lyophilized, giving the desired amide form of the polypeptides.

To obtain the ester form of betacellulin muteins, the α-carboxyl groups of the amino acids on the carboxyl terminal undergo condensation with a desired alcohol to produce an amino acid ester, and the desired ester form of the polypeptides can then be obtained in the same manner as the amide form.

Examples of DNA encoding the betacellulin muteins in the present invention include any DNA comprising DNA encoding (1) a betacellulin mutein in which 1 to 40 amino acid residues from the N terminal of the betacellulin may be deleted, and 1 to 4 amino acid residues of the first through fourth amino acid residues from the C terminal, including the Leu at 3 from the C terminal and the Asp at 4 from the C terminal, may be deleted or substituted with other amino acid residues or other peptide chains, (2) a betacellulin mutein in which 1 to 30 amino acid residues from the N terminal of the betacellulin may be deleted, and 1 to 5 amino acid residues may be inserted between the $22^{nd}$ and $23^{rd}$ amino acid residues from the C terminal, and (3) a betacellulin mutein having an amino acid sequence represented by SEQ ID NO: 45. Specific examples include those with a base sequence encoding a betacellulin mutein containing an amino acid sequence represented by SEQ ID NOs: 1 through 14, SEQ ID NO: 37, SEQ ID NO: 38, SEQ ID NO: 44, SEQ ID NO: 45, and SEQ ID NO: 46 in the present invention.

More specific examples include (1) DNA containing DNA with a base sequence represented by SEQ ID NOs: 15 through 28 as the DNA encoding betacellulin mutein having an amino acid sequence represented by SEQ ID NOs: 1 through 14, (2) DNA containing DNA with a base sequence represented by SEQ ID NOs: 42 and 43 as the DNA coding a for betacellulin mutein having an amino acid sequence represented by SEQ ID NOs: 37 and 38, (3) DNA containing DNA with a base sequence represented by SEQ ID NOs: 47 through 49, (4) DNA from mammals hybridizing with a sequence in (1) through (3) above under stringent conditions, and (5) DNA which does not form hybrids with the sequences specified in (1) through (4) because of genetic code degeneracy but which codes for a polypeptide having the same amino acid sequence. Hybridization can be performed by publicly known methods or modification thereof. The stringent conditions described above include, for example, a temperature of 42° C., 50% formamide, 4×SSPE (1×SSPE=150 mM NaCl, 10 mM $NaH_2PO4$ $H_2O$, 1 mM EDTA, pH 7.4), 5×Denhardt's solution, and 0.1% SDS.

Expression vectors for the betacellulin muteins of the present invention, which are used when the betacellulin muteins of the present invention are manufactured by culturing the transformants comprising DNA encoding betacellulin, can be manufactured, for example, by (1) excising target DNA fragments from the DNA encoding a betacellulin mutein of the present invention, and (2) ligating the DNA fragments downstream of a promoter in a suitable expression vector.

Examples of vectors include *E. coli* plasmids (e.g., pBR322, pBR325, pUC12, and pUC13), *Bacillus subtilis* plasmids (e.g., pUB110, pTP5, and pC194), yeast plasmids (e.g., pSH19 and pSH15), bacteriophages such as λ phages, and animal viruses such as retroviruses, vaccinia viruses, and baculoviruses.

Examples of promoters which may be used include any suitable promoters corresponding to the host used to express the gene.

When the host is an animal cell during transformation, it can be beneficial to use an SV40-derived promoter, retrovirus promoter, metallothionein promoter, heat shock promoter, cytomegalovirus promoter, SRα promoter, or the like. Preferred examples for *E. coli* hosts include the trp promoter, T7 promoter, lac promoter, recA promoter, λPL promoter, 1pp promoter, and the like, preferred examples for Bacillus hosts include the SPO1 promoter, SPO2 promoter, penP promoter, and the like, and preferred examples for yeast hosts include the PHO5 promoter, PGK promoter, GAP promoter, ADH1 promoter, GAL promoter, and the like. When the host is an insect cell, polyhedrin promoters and P10 promoters, etc. are preferred.

In addition to the above, expression vectors can also include enhancers, splicing signals, polyA signals, selection markers, SV40 origin of replication (henceforth, sometimes also referred to as SV40ori), and the like as desired. Examples of selection markers include the dihydrofolate reductase (dhfr) gene (methotrexate (MTX) resistance), the ampicillin resistance gene (Amp$^r$), and the neomycin resistance gene (G418 resistance, sometimes referred to as Neo). Thymidine-free media can be used for selection, particularly in cases where the DHFR gene is used as the selection marker with CHO (dhfr$^-$) cells.

A signal sequence adapting the host may be added to the N terminal side of the betacellulin mutein as needed. Preferred examples include a phoA signal sequence, OmpA signal sequence, or the like for *E. coli* hosts. Preferred examples include an α-amylase signal sequence, subtilisin signal sequence or the like for Bacillus hosts. Preferred examples include a mating factor α(MFα) signal sequence, invertase signal sequence, or the like for yeast hosts. Preferred examples include an insulin signal sequence, α-interferon signal sequence, antibody molecule signal sequence, or the like for animal cell hosts.

A vector constructed in this manner containing DNA encoding a betacellulin mutein, can be used to manufacture transformants.

Hosts which can be used include, for example, *E. coli*, Bacillus, yeasts, insects or insect cells, and animal cells.

Examples of *E. coli* include *E. coli* K12 DH1 (*Proc. Natl. Acad. Sci. USA*), 60:160 (1968)), JM103 (*Nucleic Acids Research*, 9:309 (1981)), JA221 (*Journal of Molecular Biology*, 120:517 (1978)), HB101 (*Journal of Molecular Biology*, 41:459 (1969)), C600 (*Genetics*, 39:440 (1954)), and MM294 (*Proc. Natl. Acad. Sci. USA*, 73:4174 (1976)).

Examples of Bacillus include *Bacillus subtilis* MI114 (*Gene*, 24:255 (1983)), and 207-21 (*Journal of Biochemistry*, 95:87 (1984)).

Examples of yeasts include *Saccharomyces cerevisiae* AH22, AH22R$^-$, NA87-11A, DKD-5D, and 20B-12.

Examples of insects include silkworm larvae (Maeda et al., *Nature*, 315:592 (1985)).

Examples of insect cells include, in the case of the ACNPV virus, established cell lines derived from larvae of *Spodoptera frugiperda* (Sf cells), MG1 cells derived from Trichoplusia ni mid-gut cells, High Five™ cells derived from Trichoplusia ni ovarian cells, cells derived from *Mamesira brassicae*, and cells derived from *Estigmena acrea*. Examples for when the virus is BmNPV include established cell lines derived from *Bombyx Mori* N (BmN cells). Examples of Sf cells include Sf9 cells (ATCC CRL1711) and Sf21 cells (J. L. Vaughn et al., in Vitro, Vol. 13, pp. 213–217 (1977)).

Examples of animal cells include monkey COS-7 cells, Vero cells, Chinese hamster cells CHO, DHFR gene-deficient Chinese hamster cells CHO (dhfr$^-$CHO cells), mouse L cells, mouse 3T3 cells, mouse myeloma cells, human HEK293 cells, human FL cells, 293 cells, C127 cells, BALB3T3 cells, and Sp-2/O cells.

*E. coli* can be transformed, for example, by a method described in *Proc. Natl. Acad. Sci. USA*, 69:2110 (1972) or *Gene*, 17:107 (1982).

Bacillus can be transformed, for example, by a method described in *Molecular & General Genetics*, 168:111 (1979).

Yeasts can be transformed, for example, by a method described in *Proc. Natl. Acad. Sci. USA*, 75:1929 (1978).

Insect cells and insects can be transformed, for example, by a method described in *Bio/Technology*, 6, pp. 47–55 (1988).

Animal cells can be transformed, for example, by a method described in *Virology*, 52:456 (1973).

Examples of methods for introducing expression vectors into cells include lipofection method (P. L. Felgner et al. in *Proceedings of the National Academy of Sciences of the United States of America*, Vol. 84, p. 7413 (1987)), calcium phosphate method (F. L. Graham and A. J. van der Eb in *Virology*, Vol. 52, pp. 456–467 (1973)), electroporation (E. Nuemann et al. in *EMBO J.*, Vol. 1, pp. 841–845 (1982)) and the like.

Transformants which have been transformed in expression vectors containing DNA encoding the betacellulin muteins of the present invention can be obtained in this manner.

In one method for stable expression of the betacellulin muteins of the present invention using animal cells, cells incorporating an expression vector introduced into the aforementioned animal cells to chromosome are selected by clone selection. Specifically, transformants are selected using the aforementioned selection markers as indicators. It is also possible to obtain stable animal cell lines with a high expression capacity for the betacellulin muteins of the present invention etc. through repeated clone selection of animal cells obtained using selection markers in this manner. When a dhfr gene is used as a selection marker, culture can be carried out as the MTX concentration is gradually increased, and resistant strains can be selected so that intracellular amplification of DNA encoding the betacellulin muteins of the present invention together with the dhfr gene gives an animal cell line with even higher expression.

The betacellulin muteins of the present invention can be manufactured by culturing the aforementioned transformants under conditions allowing the expression of DNA encoding the betacellulin muteins of the present invention, and producing and accumulating the betacellulin muteins of the present invention.

When culturing transformants with *E. coli* or Bacillus hosts, liquid media are suitable for the culture, and can contain carbon sources, nitrogen sources, inorganic material, and other materials necessary for the growth of the transformants. Carbon sources include glucose, dextrins, soluble starches, and sucrose, and nitrogen sources include inorganic or organic substances such as ammonium salts, nitrates, corn steep liquor, peptone, casein, meat extract, soybean cake, and potato extract. Examples of inorganic materials include calcium chloride, sodium dihydrogen phosphate, and magnesium chloride. Yeasts, vitamins, growth promoting factors, and the like may also be added. The medium pH is preferably about 5 to 8.

A preferred media for culturing *E. coli* is M9 medium containing glucose and casamino acid (Miller, *Journal of Experiments in Molecular Genetics*, pp. 431–433, Cold Spring Harbor Laboratory, New York (1972)). A chemical such as 3β-indoleacrylic acid can be added to enhance the promoter as needed.

In cases where the host is *E. coli*, the culture usually takes about 3 to 24 hours at about 15 to 43° C. The culture can be aerated or stirred as needed.

In cases where the host is Bacillus, the culture usually takes about 6 to 24 hours at about 30 to 40° C. The culture can be aerated or stirred as needed.

Examples of media for the culture of transformants with yeast hosts include Burkholder minimum medium (K. L.

Bostian et al., *Proc. Natl. Acad. Sci. USA*, Vol. 77, 4505 (1980), and SD medium containing 0.5% casamino acid (G. A. Bitter et al., *Proc. Natl. Acad. Sci. USA*, Vol. 81, 5330 (1984). The medium pH may preferably be adjusted to between about 5 and 8. The culture usually takes about 24 to 72 hours at about 20 to 35° C. The culture can be aerated or stirred as needed.

Examples of media for the culture of transformants with insect cell hosts include Grace's Insect Medium (T. C. C. Grace, *Nature*, 195:788 (1962) suitably supplemented with additives such as 10% immobilized bovine serum. The medium pH should be adjusted to between about 6.2 and 6.4. The culture usually takes about 3 to 5 days at about 27° C. The culture can be aerated or stirred as needed.

Examples of media for the culture of transformants with animal cell hosts include MEM medium containing about 5 to 20% fetal calf serum (*Science*, 122:501 (1952), DMEM medium (*virology*, 8:396 (1959), RPMI 1640 medium (*The Journal of the American Medical Association*, 199:519 (1967), and 199 medium (*Proceedings of the Society for Biological Medicine*, 73:1 (1950). The pH may preferably be about 6 to 8. The culture was usually performed for 15 to 60 hours at about 30 to 40° C. The culture can be aerated or stirred as needed.

Particularly when CHO (dhfr$^-$) cells and dhfr genes are used as selection markers, DMEM medium containing dialyzed fetal calf serum with virtually no thymidine is preferably used.

The betacellulin muteins of the present invention can be isolated and purified from the aforementioned cultures in the following manner, for example.

When the betacellulins of the present invention are extracted from cultured bacterial cells or cells, the bacterial cells or cells are collected by a publicly known method after completion of the culture and are suspended in a suitable buffer, they are disrupted by ultrasonication, lysozyme treatment and/or by freezing and thawing, etc., and the polypeptide crude extract is then obtained by centrifugation or filtration. The buffer may also contain a protein denaturant such as urea or guanidine hydrochloride, or a surfactant such as Triton X-100 (registered trademark (™)).

When betacellulin muteins are secreted in the culture broth, the bacterial cells or cells are separated from the supernatant by a publicly known method after completion of the culture, and the supernatant is collected.

The polypeptides of the present invention contained in the extract or culture supernatant obtained in this manner can be purified by a suitable combination of publicly known methods of isolation and purification. Examples of such publicly known methods of isolation and purification include methods utilizing the degree of dissolution such as solvent precipitation or salting out, methods utilizing differences primarily in molecular weight such as dialysis, ultrafiltration, gel filtration, and SDS-polyacrylamide gel electrophoresis, methods making use of differences in charge such as ion exchange chromatography, methods utilizing specific affinity such as affinity chromatography, methods utilizing hydrophobic differences such as reverse phase HPLC, and methods utilizing differences in isoelectric point, such as isoelectric point electrophoresis and chromatofocusing.

When the resulting betacellulin muteins of the present invention are obtained in free form, they can be converted to a salt by a publicly known method or a modification thereof. Alternatively, when they are obtained in the form of a salt, they can be converted to free form or another salt by a publicly known method or a modification thereof.

Betacellulin muteins of the present invention produced by recombinants can be modified as desired through the action of suitable protein-modifying enzymes before or after purification, or the betacellulin muteins can be partially removed. Examples of protein-modifying enzymes include trypsin, chymotrypsin, arginylendopeptidase, protein kinase, and glycosidase.

The resulting betacellulin muteins may be treated in a refolding step as described in Japanese Unexamined Patent Application (Kokai) H10-191989, for example. Betacellulin muteins with an N terminal Met can be subjected to a reaction for removing the Met from the N terminal as described in Japanese Unexamined Patent Application (Kokai) H10-191989 in order to remove the N terminal Met.

The presence of the resulting betacellulin muteins of the present invention can be determined by enzyme immunoassay or the like using specific antibodies.

The betacellulin muteins or their salts in the present invention or DNA encoding the betacellulin muteins of the present invention can be used in the development of drugs for improving diseases such as diabetes (e.g., insulin-dependent diabetes (I type diabetes), etc.), pancreatic dysfunction associated with diabetes, or pancreatic dysfunction associated with senile insufficient insulin secretion, and drugs for diseases such as undifferentiated pancreatic cancer (particularly prophylactic and therapeutic drugs for diabetes (such as insulin-dependent diabetes), etc.).

Because the betacellulin muteins or their salts in the present invention or DNA encoding them have reduced EGF activity and no problems in terms of antigenicity, they can be useful as safe and low toxic drugs. The betacellulin muteins or their salts in the present invention or DNA encoding them can be used as drugs to improve diseases such as diabetes (such as insulin-dependent diabetes), pancreatic dysfunction associated with diabetes, and pancreatic dysfunction associated with insufficient insulin secretion in the elderly, and as therapeutic and prophylactic drugs for diseases such as undifferentiated pancreatic cancer.

The betacellulin muteins or salts in the present invention or DNA encoding them can be used in the conventional manner as the aforementioned drugs. For example, they can be orally administered in the form of coated or enterically coated tablets, capsules, elixirs, microcapsules, and the like, and can be parenterally administered in the form of injections such as sterile solutions with water or other pharmaceutically acceptable liquids, or suspensions. Such preparations can be manufactured, for example, by mixing the compounds or salt in unit dose formulations required for generally recognized preparations, along with physiologically permissible carriers, flavorings, excipients, vehicles, antiseptics, stabilizers, binders, and the like. The content of the active ingredient in such formulations will give a suitable dose within the indicated range.

Examples of additives which can be miscible with tablets, capsules, and the like include binders such as gelatin, corn starch, tragacanth gum, and gum arabic, excipients such as crystalline cellulose, swellings such as corn starch, gelatin, and alginic acid, lubricants such as magnesium stearate, sweeteners such as sucrose, lactose, and saccharin, and flavors such as peppermint, Akamono oil, or cherry. In the case of unit formulations in the form of capsule preparations, the material can also include a liquid carrier such as a lipid. Sterile compositions for injections can be formulated by a common method such as dissolving or suspending a naturally produced vegetable oil or the like such as sesame oil or coconut oil and the active ingredient in a vehicle such as water for injection.

Examples of aqueous solutions for injection include physiological saline, isotonic liquids containing glucose or other adjuvants (such as D-sorbitol, D-mannitol, and sodium chloride). Suitable dissolving aids such as alcohols (such as ethanol), polyalcohols (such as propylene glycol and polyethylene glycol), and nonionic surfactants (such as Polysorbate 80™ and HCO-50) can also be used. Examples of oleaginous solutions include sesame oil and soybean oil. Examples of dissolution aids include benzyl benzoate and benzyl alcohol.

Buffers (such as phosphate buffers and sodium acetate buffers), analgesics (such as benzalkonium and procaine hydrochloride), stabilizers (such as human serum albumin and polyethylene glycol), preservatives (such as benzyl alcohol and phenol), antioxidants, and the like can also be blended. Injections are usually packaged in suitable ampules.

The resulting preparation is safe and has low toxicity, and can thus be administered, for example, to humans and mammals (such as mice, rats, guinea pigs, rabbits, goats, pigs, cows, cats, dogs, monkeys, sacred baboons, and chimpanzees).

The dosage of the betacellulin mutein or salt thereof in the present invention varies depending on the subjects condition, etc. The orally administered dosage for patients with adult diabetes (per 60 kg body weight) is generally about 0.1 to 100 mg per day, preferably about 1.0 to 50 mg, and even more preferably about 1.0 to 20 mg. The parenterally administered dosage at a time varies depending on the purpose of administration, the target organ, the subject's condition, the method of administration, and so forth. Intravenous injections, for example, for patients with adult diabetes (per 60 kg body weight) are generally about 0.01 to 30 mg per day, preferably about 0.1 to 20 mg, and even more preferably about 0.1 to 10 mg. The dosage for other mammals can also be calculated in terms of 60 kg.

Abbreviations for bases, amino acids, and the like in the Specification and figures are based on the IUPAC-IUB Commission on Biochemical Nomenclature and on abbreviations common in the field. Examples are given below. Optical isomers of amino acids are the L form, unless otherwise specified.

DNA: deoxyribonucleic acid
cDNA: complementary deoxyribonucleic acid
A: adenine
T: thymine
G: guanine
C: cytosine
EDTA: ethyleendiaminetetraacetic acid
APMSF: (p-amidinophenyl) methanesulfonylfluoride hydrochloride
SDS: sodium dodecylsulfate
TFA: trifluoroacetic acid
Gly: gylcine
Ala: alanine
Val: valine
Leu: leucine
Ile: isoleucine
Ser: serine
Thr: threonine
Cys: cysteine
Met: methionine
Glu: glutamic acid
Asp: aspartic acid
Lys: lysine
Arg: arginine
His: histidine
Phe: phenylalanine
Tyr: tyrosine
Trp: tryptophan
Pro: proline
Asn: asparagine
Gln: glutamine
NMP: N-methylpyrrolidone Substituents, protection groups, and reagents used in the Specification are represented by the following symbols.

Me: methyl group
Et: ethyl group
Bu: butyl group
Ph: phenyl group
TC: thiazolidine-4(R)-carboxamide group
Bom: benzyloxymethyl
PAM: phenylacetamide methyl
Tos: p-toluenesulfonyl
HONB: N-hydroxy-5-norbornene-2,3-dicarboxyimide
Bzl: benzyl group
Z: benzyloxycarbonyl group
Br—Z: 2-bromobenzyloxycarbonyl group
Cl—Z: 2-chlorobenzyloxycarbonyl group
Boc: t-butyloxycarbonyl group
HOBt: 1-hydroxybenztriazole
DCC: N,N'-dicyclohexylcarbodiimide
TFA: trifluoroacetic acid
Fmoc: N-9-fluorenylmethoxycarbonyl group
DNP: dinitrophenyl group
Bum: tertiary butoxymethyl group
Trt: trityl group The SEQ ID NOs: in the Sequence Listing in the specification indicate the following sequences.

SEQ ID NO: 1
  amino acid sequence of betacellulin mutein (BTC1–77) of the present invention
SEQ ID NO: 2
  amino acid sequence of betacellulin mutein (BTC1–76) of the present invention
SEQ ID NO: 3
  amino acid sequence of betacellulin mutein (BTC31–77) of the present invention
SEQ ID NO: 4
  amino acid sequence of betacellulin mutein (BTC31–76) of the present invention
SEQ ID NO: 5
  amino acid sequence of betacellulin mutein (BTC1–76, 78–80) of the present invention
SEQ ID NO: 6
  amino acid sequence of betacellulin mutein (BTC1–76, 78, 79) of the present invention
SEQ ID NO: 7
  amino acid sequence of betacellulin mutein (BTC1–76, 78) of the present invention
SEQ ID NO: 8
  amino acid sequence of betacellulin mutein (BTC1–77, 79, 80) of the present invention SEQ ID NO: 9
  amino acid sequence of betacellulin mutein (BTC1–77, 80) of the present invention
SEQ ID NO: 10
  amino acid sequence of betacellulin mutein (BTC31–76, 78–80) of the present invention
SEQ ID NO: 11
  amino acid sequence of betacellulin mutein (BTC31–76, 78, 79) of the present invention
SEQ ID NO: 12
  amino acid sequence of betacellulin mutein (BTC31–76, 78) of the present invention
SEQ ID NO: 13
  amino acid sequence of betacellulin mutein (BTC31–77, 79, 80) of the present invention
SEQ ID NO: 14
  amino acid sequence of betacellulin mutein (BTC31–77, 79) of the present invention
SEQ ID NO: 15
  base sequence of cDNA encoding betacellulin mutein represented by the amino acid sequence of SEQ ID NO: 1
SEQ ID NO: 16
  base sequence of cDNA encoding betacellulin mutein represented by the amino acid sequence of SEQ ID NO: 2
SEQ ID NO: 17
  base sequence of cDNA encoding betacellulin mutein represented by the amino acid sequence of SEQ ID NO: 3
SEQ ID NO: 18
  base sequence of cDNA encoding betacellulin mutein represented by the amino acid sequence of SEQ ID NO: 4
SEQ ID NO: 19
  base sequence of cDNA encoding betacellulin mutein represented by the amino acid sequence of SEQ ID NO: 5
SEQ ID NO: 20
  base sequence of cDNA encoding betacellulin mutein represented by the amino acid sequence of SEQ ID NO: 6
SEQ ID NO: 21
  base sequence of cDNA encoding betacellulin mutein represented by the amino acid sequence of SEQ ID NO: 7
SEQ ID NO: 22
  base sequence of cDNA encoding betacellulin mutein represented by the amino acid sequence of SEQ ID NO: 8
SEQ ID NO: 23
  base sequence of cDNA encoding betacellulin mutein represented by the amino acid sequence of SEQ ID NO: 9
SEQ ID NO: 24
  base sequence of cDNA encoding betacellulin mutein represented by the amino acid sequence of SEQ ID NO: 10
SEQ ID NO: 25
  base sequence of cDNA encoding betacellulin mutein represented by the amino acid sequence of SEQ ID NO: 11
SEQ ID NO: 26
  base sequence of cDNA encoding betacellulin mutein represented by the amino acid sequence of SEQ ID NO: 12
SEQ ID NO: 27
  base sequence of cDNA encoding betacellulin mutein represented by the amino acid sequence of SEQ ID NO: 13
SEQ ID NO: 28
  base sequence of cDNA encoding betacellulin mutein represented by the amino acid sequence of SEQ ID NO: 14
SEQ ID NO: 29
  base sequence for primer 1 used in Examples 1 and 4 below
SEQ ID NO: 30
  base sequence for primer 2 used in Examples 1 and 4 below
SEQ ID NO: 31
  base sequence for primer RI-1 used in Examples 10 and 27 below
SEQ ID NO: 32
  base sequence for primer RI-3 used in Examples 10 and 27 below
SEQ ID NO: 33
  base sequence for primer RI-1Cla used in Examples 10 and 27 below
SEQ ID NO: 34
  base sequence for primer RI-3Xho used in Examples 10 and 27 below
SEQ ID NO: 35
  amino acid sequence for betacellulin
SEQ ID NO: 36
  base sequence of cDNA encoding betacellulin
SEQ ID NO: 37
  amino acid sequence of betacellulin mutein (BTC2–76) of the present invention
SEQ ID NO: 38
  amino acid sequence of betacellulin mutein (BTC24–76) of the present invention
SEQ ID NO: 39
  base sequence of primer 3 used in Example 13 below
SEQ ID NO: 40
  base sequence of primer 4 used in Examples 13 and 16 below
SEQ ID NO: 41
  base sequence of primer 5 used in Example 16 below
SEQ ID NO: 42
  base sequence of cDNA encoding betacellulin mutein represented by amino acid sequence of SEQ ID NO: 37
SEQ ID NO: 43
  base sequence of cDNA encoding betacellulin mutein represented by amino acid sequence of SEQ ID NO: 38
SEQ ID NO: 44
  amino acid sequence of betacellulin mutein (BTC31–58, Asn, Pro, Ser. 59–80) of the present invention
SEQ ID NO: 45
  amino acid sequence of betacellulin mutein (Asn, Ser, Asp, Ser, Glu, BTC38–80) of the present invention
SEQ ID NO: 46
  amino acid sequence of betacellulin mutein (BTC1–58, Asn, Pro, Ser. obliterated-80) of the present invention
SEQ ID NO: 47
  base sequence of cDNA encoding betacellulin mutein represented by the amino acid sequence of SEQ ID NO: 46

SEQ ID NO: 48
  base sequence of cDNA encoding betacellulin mutein represented by the amino acid sequence of SEQ ID NO: 44
SEQ ID NO: 49
  base sequence of cDNA encoding betacellulin mutein represented by the amino acid sequence of SEQ ID NO: 45
SEQ ID NO: 50
  base sequence of primer BT-95h used in Reference Example 1 and Example 22 below
SEQ ID NO: 51
  base sequence of primer BT-94h used in Reference Example 1 and Example 23 below
SEQ ID NO: 52
  base sequence of primer PET-1 used in Example 22 below
SEQ ID NO: 53
  base sequence of primer BTC-1 used in Example 22 below
SEQ ID NO: 54
  base sequence of primer BTC-2 used in Example 22 below
SEQ ID NO: 55
  base sequence of primer BTC-3 used in Example 22 below
SEQ ID NO: 56
  base sequence of primer BTC-7 used in Example 23 below
SEQ ID NO: 57
  the $1^{st}$ to $40^{th}$ amino acid sequence from N-terminal of betaceuulin
SEQ ID NO: 58
  the $41^{st}$ to $76^{th}$ amino acid sequence from N-terminal of betacellulin
SEQ ID NO: 59
  the $1^{st}$ to $37^{th}$ amino acid sequence from N-terminal of betacellulin
SEQ ID NO: 60
  the $38^{th}$ to $76^{th}$ amino acid sequence from N-terminal of betacellulin
SEQ ID NO: 61
  the $2^{nd}$ to $76^{th}$ amino acid sequence from N-terminal of betacellulin
SEQ ID NO: 62
  the $1^{st}$ to $23^{rd}$ amino acid sequence from N-terminal of betacellulin
SEQ ID NO: 63
  the $24^{th}$ to $76^{th}$ amino acid sequence from N-terminal of betacellulin
SEQ ID NO: 64
  the $1^{st}$ to $30^{th}$ amino acid sequence from N-terminal of betacellulin The transformant *E. coli* MM294 (DE3)/pTCIIBTC77 obtained in Example 1 below was registered under the Accession No. FERM BP-6584 on Nov. 24, 1998 at the National Institute of Bioscience and Human Technology (NIBH), Agency of Industrial Science and Technology, Ministry of International Trade and Industry. It was also registered under the Accession No. IFO 16214 on Nov. 2, 1998 at the Institute for Fermentation (IFO).

The transformant *E. coli* MM294 (DE3)/pTCIIBTC76 obtained in Example 4 below was registered under the Accession No. FERM BP-6583 on Nov. 24, 1998 at the National Institute of Bioscience and Human Technology, Agency of Industrial Science and Technology, Ministry of International Trade and Industry. It was also registered under the Accession No. IFO 16213 on Nov. 2, 1998 at the Institute for Fermentation (IFO).

The transformant *E. coli* MM294 (DE3)/pTCIIBTC2–76 obtained in Example 13 below was registered under the Accession No. FERM BP-6948 on Nov. 24, 1999 at the National Institute of Bioscience and Human Technology, Agency of Industrial Science and Technology, Ministry of International Trade and Industry. It was also registered under the Accession No. IFO 16334 on Nov. 9, 1999 at the Institute for Fermentation (IFO).

The transformant *E. coli* MM294 (DE3)/pTCIIBTC24–76 obtained in Example 16 below was registered under the Accession No. FERM BP-6949 on Nov. 24, 1999 at the National Institute of Bioscience and Human Technology, Agency of Industrial Science and Technology, Ministry of International Trade and Industry. It was also registered under the Accession No. IFO 16335 on Nov. 9, 1999 at the Institute for Fermentation (IFO).

The *E. coli* MM294 (DE3)/pLysS, pTB1516 with the plasmid pTB1516obtained in Reference 1 below was registered under the Accession No. FERM BP-3836 on Apr. 21, 1992 at the National Institute of Bioscience and Human Technology, Agency of Industrial Science and Technology, Ministry of International Trade and Industry (NIBH). It was also registered under the Accession No. IFO 15282 on Apr. 16, 1992 at the Institute for Fermentation.

Examples and references are given below to illustrate the present invention in further detail, but the scope of the present invention is not limited by these examples.

EXAMPLE 1

Construction of 77 residue (lacking three C terminal residues) betacellulin expression strain A 77 residue (lacking three C terminal residues) betacellulin expression plasmid was constructed in the following manner (FIG. 1).

The 77 residue (lacking three C terminal residues) betacellulin structural gene was amplified by PCR from the pB041 betacellulin expression plasmid (Seno et al, *Growth Factors*, 13:181 (1996)) using a primer 1 (5'-CATATGGATGGGAATTCCACCAGAAGTCCTG; SEQ ID NO: 29) having an NdeI cleavage site and start codon adjacent upstream of the structural gene and a primer 2 (5-GGATCCCTAGTCAACTCTCTCACACCTTGCTCC; SEQ ID NO: 30) having a stop codon and BamHI cleavage site after the aspartic acid at 77. The gene thus amplified by PCR was ligated to the pCR2.1 vector using a TA original cloning kit (by Invitrogen) to prepare pCR2.1/BTC77. This was introduced to *E. coli* JM 109, and transformants were selected using ampicillin resistance and β-galactosidase activity as indicators. Transformants having pCR2.1/BTC77 were cultured, and pCR2.1/BTC77 was prepared using a QIAprep8 Miniprep kit (by Qiagen).

pBR322 was digested with NdeI, the ends were blunted with T4 DNA polymerase (DNA Blunting kit, by Takara Shuzo), and pBRdesNde lacking the NdeI recognition site was prepared by religation. pET3c was digested with Bgl II-EcoRV, approximately 0.26 kbp fragments were recovered, the ends were blunted with T4 DNA polymerase, and pBR/T7 desNde was produced by ligation with the ScaI fragment of pBRdesNde. pBR322desBam lacking the BamHI recognition site of pBR322 was prepared by site-directed mutagenesis (Quick Change, by Stratagene). The SphI-EcoRV fragment of pBR322desBam was ligated with the SphI-EcoRV fragment of pBR/T7desNde, giving the tetracycline resistance expression vector pTCII. pCR2.1/BTC77 was digested with NdeI and BamHI and followed by running agarose electrophoresis, and approximately 240 bp of the 77 residue betacellulin structural gene was recovered using the QIAquick Spin Purification kit (by Qiagen). The expression vector PTCII was digested with NdeI and BamHI and followed by running agarose electrophoresis, and approximately 4.6 kbp bands were similarly recovered. The 77 residue betacellulin structural gene was ligated with the NdeI-BamHI fragment of the pTCII expression vector and then incorporated into E. coli JM109 for selection of transformants by tetracycline resistance, and plasmids were again recovered from the strain, giving the expression plasmid pTCIIBTC77.

The resulting pTCIIBTC77 was incorporated into E. coli MM294 (DE3) for selection of transformants by tetracycline resistance, giving the 77 residue betacellulin expression line MM294 (DE3)/pTCIIBTC77.

EXAMPLE 2

Culture of 77 residue betacellulin expression strain

The 77 residue betacellulin expression strain MM294 (DE3)/pTCIIBTC77 was cultured for 16 hours at 30° C. in 1 L of LB medium (1% peptone, 0.5% yeast extract, 0.5% sodium chloride) containing 10 mg/L tetracycline. 150 mL of the resulting culture was used to inoculate 2 L jar fermenters containing 1.5 L primary fermentation medium (1.68% sodium monohydrogen phosphate, 0.3% sodium dihydrogen phosphate, 0.1% ammonium chloride, 0.05% sodium chloride, 0.024% magnesium sulfate, 0.02% Nupol LB-625, 0.0005% thiamine hydrochloride, 1.5% glucose, 1.0% casamino acid, 1.0% yeast extract) and the culture was started with aeration and agitation under conditions of 500 rpm, an air flow rate of 2 L/min, and a o temperature of 37° C. When the turbidity of the culture reached about 1200 Klett units, 5.95 mg/L isopropyl-β-D-thiogalactopyranoside (IPTG) was added. 0.75% glucose was added 1 and 2.5 hours after IPTG addition, and the culture continued until 9 hours after the start of culture. The culture broth was centrifuged for 30 minutes at 10,000 rpm to collect the cells.

EXAMPLE 3

Purification of Met-77 Residue Betacellulin 10 mL of 0.1 M Tris-HCl (pH 8.0) containing 1 mM EDTA, 1 mM APMSF, and 7 M guanidine hydrochloride was added to 5 g of cells obtained in Example 2, the mixture was stirred over night at 4° C. for extraction, and then centrifuged (20 min at 10,000 rpm). 250 mL of 50 mM Tris-HCl (pH 8.0) containing 0.5 mM oxidized type glutathione, 1 mM reduced type glutathione, 1 mM EDTA, 0.1 M arginine hydrochloride, and 2 M urea was added to 10 mL of the resulting supernatant for refolding overnight at 4° C., followed by centrifugation (20 min at 10,000 rpm), resulting in 260 mL of supernatant. The supernatant was concentrated using a YM3 membrane (fraction molecular weight: 3000, by Millipore). 120 mL of 2 M urea was added to 80 mL of the desalted concentrate, and the pH was then adjusted to 5.0 with hydrochloric acid. Supernatant obtained upon 20 min of centrifugation at 10,000 rpm was adsorbed at a flow rate of 10 mL/min onto a SP-Toyopearl 650 M column (2.2 cm×12 cm, by Tosoh) equilibrated with 50 mM sodium acetate buffer (pH 5.0), and the column was washed with the buffer used for equilibration, followed by elution with a linear gradient of 0 to 1.0 M sodium chloride. Fractions containing the Met-77 residue betacellulin were collected, one third of the fraction was adsorbed to a C4P-50 column (1.0 cm×25 cm, by Showa Denko) equilibrated with 0.1% trifluoroacetic acid, and the Met-77 residue betacellulin was eluted with a linear gradient of 13.5 to 21.2% acetonitrile. Eluate obtained by two more of the same operations was dialyzed against 0.02% trifluoroacetic acid and lyophilized. The lyophilized powder was dissolved in 10 mL distilled water, allowed to flow through an AG1-X8 column (1.0 cm×10 cm, by Nippon Biorad) treated with acetic acid, and then again lyophilized, giving 8 mg of Met-77 residue betacellulin.

EXAMPLE 4

Figure 2:
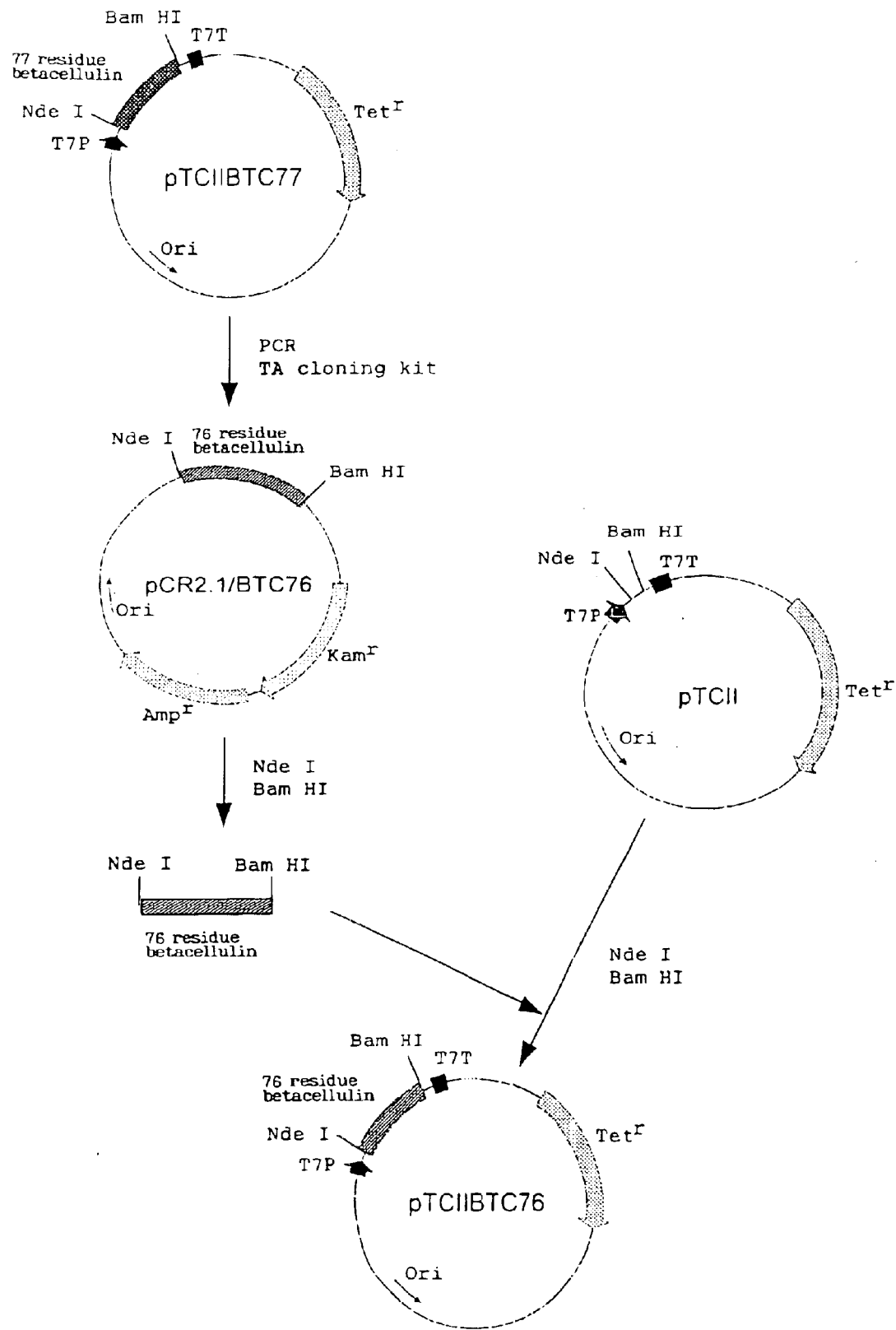
FIG. 2 illustrates the construction of an expression plasmid for 76 residue betacellulin (with four c terminal residues deleted)

Construction of 76 residue (lacking four C terminal residues) betacellulin expression plasmid A 76 residue (lacking four C terminal residues) betacellulin expression plasmid was constructed in the following manner (FIG. 2).

The 76 residue (lacling four C terminal residues) betacellulin structural gene was amplified by PCR from the pTCII/BTC77 constructed in Example 1 using primer 1 (5'-CATATGGATGGGAATTCCACCAGAAGTCCTG; SEQ ID NO: 29) having an NdeI cleavage site and start codon adjacent upstream of the structural gene and a primer 2 (5'-GGATCCCTAAACTCTCTCACACCTTGCTCCAATG; SEQ ID NO: 30) having a stop codon and BamHI cleavage site after the valine at 76. The gene thus amplified by PCR was ligated to the pCR2.1 vector using a TA original cloning kit (by Invitrogen) to prepare pCR2.1/BTC76. This was introduced to E. coli JM 109, and transformants were selected using ampicillin resistance and β-galactosidase activity as indicators. Transformants having pCR2.1/BTC76 were cultured, and pCR2.1/BTC76 was prepared using a QIAprep8 Miniprep kit (by Qiagen).

pCR2.1/BTC76 was digested with NdeI and BamHI and followed by running agarose electrophoresis, and approximately 240 bp of the 76 residue betacellulin structural gene was recovered using the QIAquick Spin Purification kit (by Qiagen). The expression vector pTCII obtained in Example 1 was digested with NdeI and BamHI and followed by running agarose electrophoresis, and approximately 4.6 kbp bands were similarly recovered. The 76 residue betacellulin structural gene was ligated with the NdeI-BamHI fragment of the PTCII expression vector and then incorporated into E. coli JM109 for selection of transformants by tetracycline resistance, and plasmids were again recovered from the strain, giving the expression plasmid pTCIIBTC76.

The resulting pTCIIBTC76 was incorporated into E. coli MM294 (DE3) for selection of transformants by tetracycline resistance, giving the 76 residue betacellulin expression strain MM294 (DE3)/pTCIIBTC76.

EXAMPLE 5

Culture of 76 Residue Betacellulin Expression Line

The 76 residue betacellulin expression line MM294 (DE3)/pTCIIBTC76 was cultured for 16 hours at 30° C. in 1 L of LB medium (1% peptone, 0.5% yeast extract, 0.5% sodium chloride) containing 10 mg/L tetracycline. The resulting culture was used to inoculate 50 L fermenter tanks containing 20 L primary fermentation medium (1.68% sodium monohydrogen phosphate, 0.3% sodium dihydrogen phosphate, 0.1% ammonium chloride, 0.05% sodium chloride, 0.024% magnesium sulfate, 0.02% Nupol LB-625, 0.0005% thiamine hydrochloride, 1.5% glucose, 1.0% casamino acid, 1.0% yeast extract) and the culture was started with aeration and agitation under the conditions of 210 rpm, an air flow rate of 20 L/min, and a temperature of 37° C. When the turbidity of the culture reached about 1200 Klett units, 5.95 mg/L isopropyl-β-D-thiogalactopyranoside (IPTG) was added. 0.75% glucose was added 2 and 3.5 hours after IPTG addition, and the culture continued until 11 hours after the start of culture. The culture broth was centrifuged for 30 minutes at 10,000 rpm to collect 540 g of the cells.

EXAMPLE 6

Purification of Met-76 Residue Betacellulin 1.0 L of 0.1 M Tris-HCl (pH 8.0) containing 1 mM EDTA, 1 mM APMSF, and 7 M guanidine hydrochloride was added to 375 g of cells obtained in Example 5, the mixture was stirred over night at 4° C. for extraction, and then centrifuged (20 min at 10,000 rpm). 19 L of 50 mM Tris-HCl (pH 8.0) containing 0.5 mM oxidized type glutathione, 1 mM reduced type glutathione, 1 mM EDTA, 0.1 M arginine hydrochloride, and 2 M urea was added to 1.0 L of the resulting supernatant for refolding overnight at 4° C., followed by centrifugation (20 min at 10,000 rpm), resulting in 20 L supernatant. The supernatant was concentrated using a Pelicon cassette system (fraction molecular weight: 5000, by Millipore). 13.2 L of 2 M urea was added to 3.3 L of the desalted concentrate, and the pH was then adjusted to 5.0 with hydrochloric acid. The concentrate was adsorbed at a flow rate of 30 mL/min onto a Poros 50HS column (2.2 cm×12 cm, by Nippon Perceptive) equilibrated with 50 mM sodium acetate buffer (pH 5.0), and the column was washed with the buffer used for equilibration, followed by elution with a linear gradient of 0.3 to 1.3 M sodium chloride. Fractions containing the 76 residue betacellulin were collected, diluted 3-fold with distilled water, then applied to a TSKgel CM-5PW column (2.15 cm×15 cm, by Tosoh) equilibrated with 50 mM sodium acetate (pH 4.5). Fractions were eluted, from the TSKgel CM-SPW column onto which the Met-76 residue betacellulin had been adsorbed, with a linear gradient of 0.24 to 0.44 M sodium chloride. Fractions containing the Met-76 residue betacellulin were collected and adsorbed to a TSKgel ODS-120T column (2.15 cm×30 cm, by Tosoh) equilibrated with 0.1% trifluoroacetic acid, and the Met-76 residue betacellulin was eluted with a linear gradient of 17 to 24% acetonitrile. The eluate was dialyzed against 0.02% trifluoroacetic acid and lyophilized. The lyophilized powder was dissolved in 10 mL distilled water, allowed to flow through an AG1-X8 column (1.0 cm×10 cm, by Nippon Biorad) treated with acetic acid, and then again lyophilized, giving 93 mg of Met-76 residue betacellulin.

EXAMPLE 7

Characterization of Betacellulin Muteins

The Met-77 residue betacellulin mutein obtained in Example 3 and the Met-76 residue betacellulin mutein obtained in Example 6 were characterized in the following manner.

a) Analysis by SDS-PAGE

Figure 3:
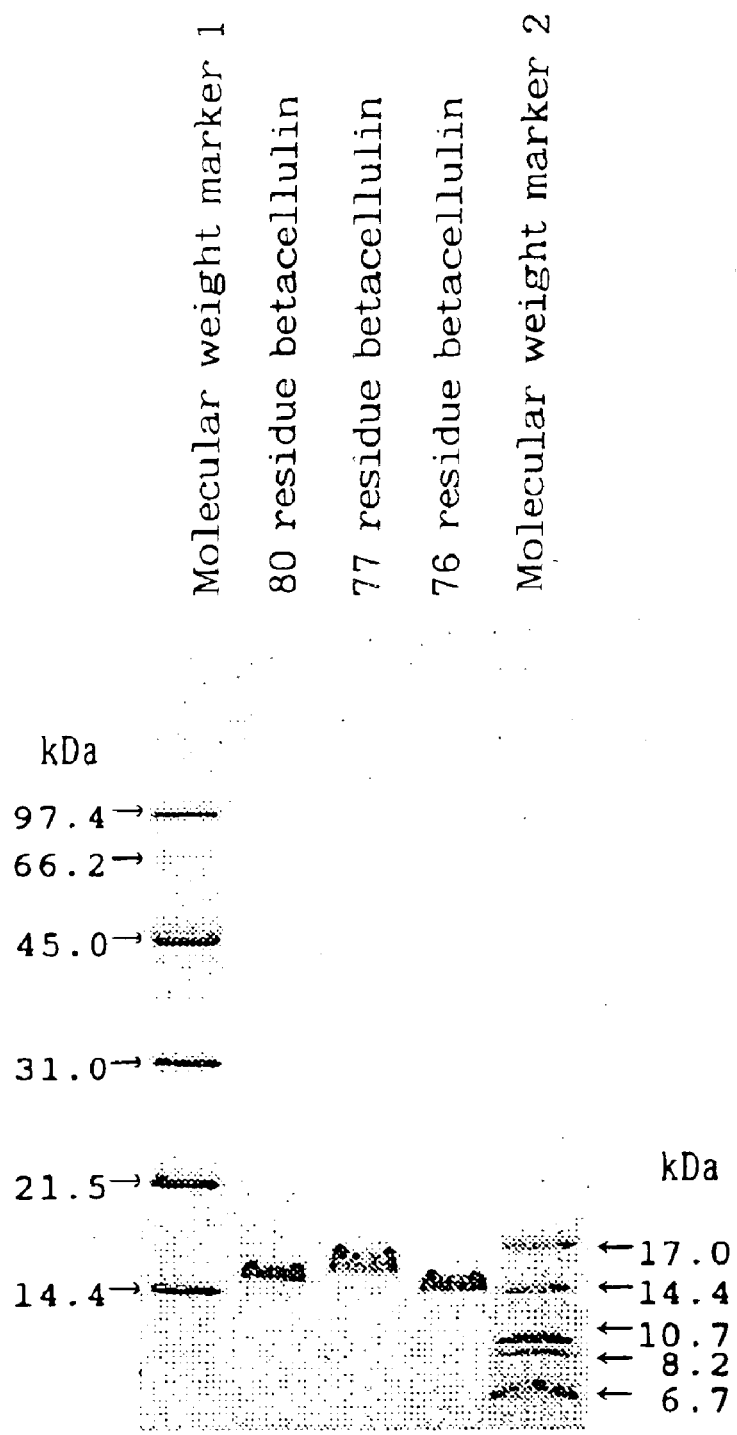
FIG. 3 illustrates the results of electrophoresis of betacellulin muteins in Example 7.

The betacellulin muteins and Met-80 residue betacellulin prepared by the method in Japanese Unexamined Patent Application (Kokai) H10-191989 were suspended in sample buffer (125 mM Tris-HCl, 1% sodium dodecylsulfate, 15% glycerol, 5% 2-mercaptoethanol, 0.005% bromophenol blue), and were electrophoresed on Multigel 15/25 (Dai'ichi Kagaku Yakuhin). Staining of the electrophoresed gel with Rapid CBB Kanto (Kanto Chemical) revealed a single band in virtually all cases (FIG. 3).

b) Analysis of Amino Acid Composition

The betacellulin muteins were hydrolyzed in the gas phase for 24 and 48 hours at 110° C. with 6 N hydrochloric acid containing 4% thioglycolic acid, and the amino acid composition was determined with an amino acid analyzer (Hitachi L-8500A Amino Acid Analyzer). The results showed that both muteins contained methionine derived from the start codon ATG, and were consistent with the amino acid composition deduced from the cDNA base sequences (Tables 1 and 2).

TABLE 1 analysis of amino acid composition of 77 residue betacellulin

|  | Number of residues per mol | Theoretical value |
| --- | --- | --- |
| Asx | 7.2 | 7 |
| Thr | 6.0 | 6 |
| Ser | 4.6 | 5 |
| Glx | 9.1 | 9 |
| Pro | 3.9 | 4 |
| Gly | 7.1 | 7 |
| Ala | 4.0 | 4 |
| Val | 3.7 | 4 |
| Met | 0.9 | 1 |
| Ile | 2.0 | 2 |
| Leu | 2.1 | 2 |
| Tyr | 3.0 | 3 |
| Phe | 2.1 | 2 |
| Lys | 5.0 | 5 |
| His | 3.0 | 2 |
| Arg | 6.8 | 7 |
| Cys | ND | 8 |

TABLE 2 analysis of amino acid composition of 76 residue betacellulin

|  | Number of residues per mol | Theoretical value |
| --- | --- | --- |
| Asx | 6.2 | 6 |
| Thr | 6.1 | 6 |
| Ser | 5.1 | 5 |
| Glx | 9.4 | 9 |
| Pro | 4.1 | 4 |
| Gly | 7.4 | 7 |
| Ala | 4.1 | 4 |
| Val | 3.8 | 4 |
| Met | 1.0 | 1 |
| Ile | 2.0 | 2 |
| Leu | 2.0 | 2 |
| Tyr | 3.1 | 3 |
| Phe | 2.1 | 2 |
| Lys | 5.0 | 5 |
| His | 2.3 | 2 |
| Arg | 7.1 | 7 |
| Cys | ND | 8 | c) Analysis of N Terminal Amino Acid Sequence

The N terminal amino acid sequence was analyzed using a gas phase protein sequencer (Applied Biosystems, Model 477A). The results showed that both muteins were consistent with the amino acid composition deduced from the cDNA base sequences. Both muteins had N terminal methionines derived from the start codon ATG just as the 80 residue type did (Tables 3 and 4).

TABLE 3

Analysis of N terminal amino acid sequence of 77 residue betacellulin

| PTH-amino acid detected (pmole) | Amino acid deduced from base sequence |
|---|---|
| 1  Met (809) | (Met) |
| 2  Asp (492) | Asp |
| 3  Gly (615) | Gly |
| 4  Asn (425) | Asn |
| 5  Ser (161) | Ser |
| 6  Thr (276) | Thr |
| 7  Arg (253) | Arg |
| 8  Ser (66) | Ser |
| 9  Pro (168) | Pro |
| 10 Glu (127) | Glu |

TABLE 4

Analysis of N terminal amino acid sequence of 76 residue betacellulin

| PTH-amino acid detected (pmole) | Amino acid deduced from base sequence |
|---|---|
| 1  Met (195) | (Met) |
| 2  Asp (213) | Asp |
| 3  Gly (413) | Gly |
| 4  Asn (292) | Asn |
| 5  Ser (99) | Ser |
| 6  Thr (151) | Thr |
| 7  Arg (198) | Arg |
| 8  Ser (54) | Ser |
| 9  Pro (149) | Pro |
| 10 Glu (79) | Glu | d) Analysis of C Terminal Amino Acids

The C terminal amino acids were determined using an amino acid analyzer (Hitachi L-8500A Amino Acid Analyzer) by gas phase hydrazine decomposition (6 hours at 100° C.). Aspartic acid was detected in the Met-77 residue betacellulin, and valine was detected in the Met-76 residue betacellulin (Tables 5 and 6).

TABLE 5

Analysis of C terminal amino acid in 77 residue betacellulin

Asp (yield: 32.5%)

TABLE 6

Analysis of C terminal amino acid in 76 residue betacellulin

Val (yield: 77.8%)

EXAMPLE 8

Assay of Growth Promoting Activity Using 3T3 Cells

As described in *Molecular Cell Biology*, 8:588 (1988), the growth promoting activity was assayed by means of the $^3$H-thymidine uptake into stationary 3T3 A31-714 Clone 4 (*International Journal of Cancer*, 12:463 (1973)).

Figure 4:
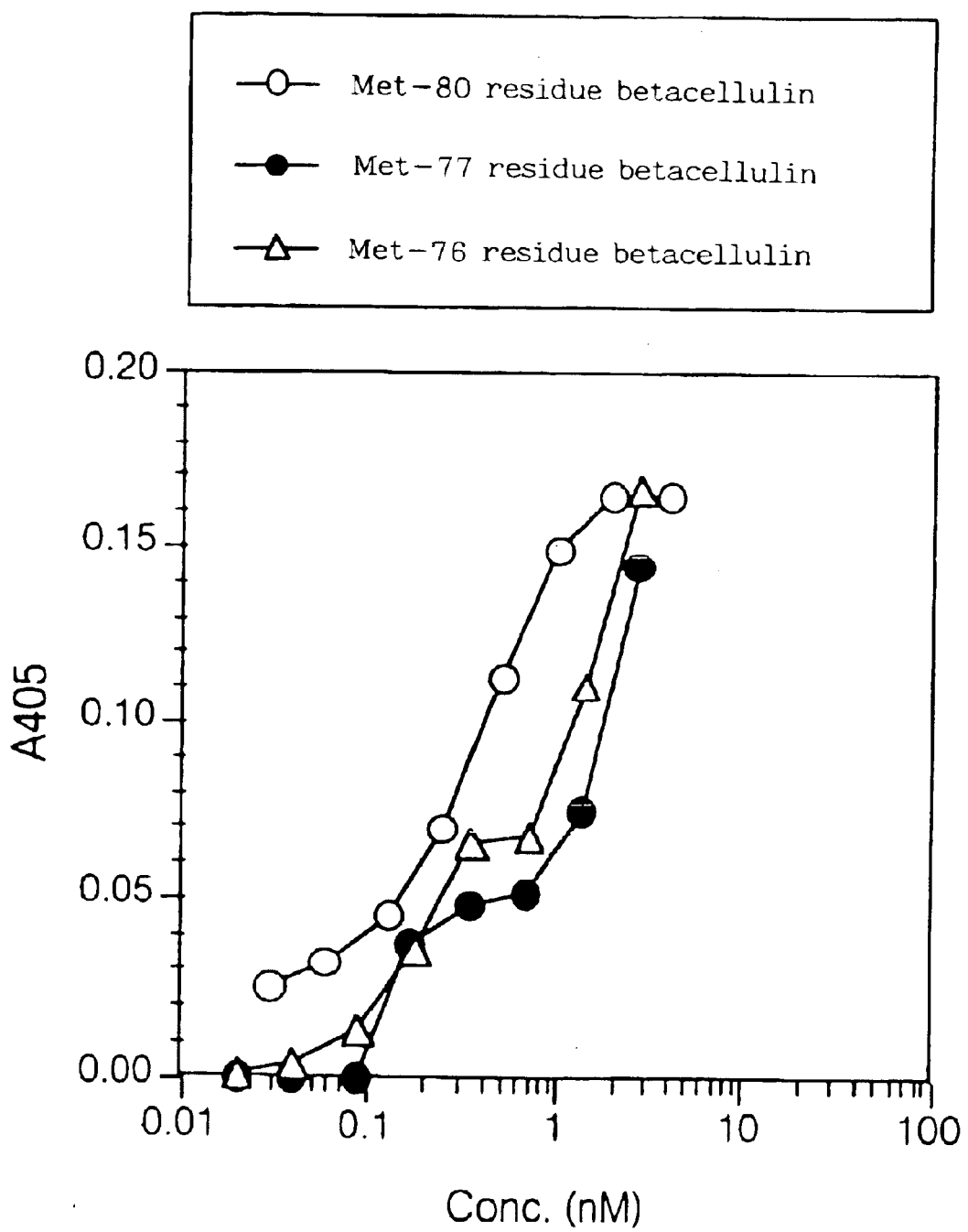
FIG. 4 illustrates the results of the cellular uptake of $^3$H-thymidine in Example 8.

Specifically, using Dulbecco's modified Eagle MEM medium containing 5% bovine serum, 100 μL 3T3 A31-714 Clone 4 suspended to 1000 cells/mL were inoculated in 96 well plates and cultivated for a day at 37° C. in carbon dioxide gas incubators (5% carbon dioxide gas, 95% air). 75 μL of supernatant was taken, and 100 μL of serum-free Dulbecco's modified Eagle MEM medium was added to adjust the serum concentration to 1%. Two more days of culture was followed by the addition of varying concentrations of the Met-77 residue betacellulin prepared in Example 3, the Met-76 residue betacellulin prepared in Example 6, and the Met-80 residue betacellulin prepared in accordance with the method described in Japanese Unexamined Patent Application (Kokai) H10-191989. 16 hours after addition of betacellulin, $^3$H-thymidine (Amersham Pharmacia Biotech) was added in an amount of 0.25 μCi/well, after 4 hours the cells were washed 3 times with PBS, 100 μL of 5% SDS was added, and the cells were lysed. The cell lysate was transferred to scintillation vials, 1 mL of Scintillator A (Wako Pure Chemicals) was added, and the uptake of $^3$H-thymidine into the cell was measured with a scintillation counter (FIG. 4).

EXAMPLE 9

Assay of β Cell Differentiation Promoting Activity Using AR42J Cells

Figure 5:
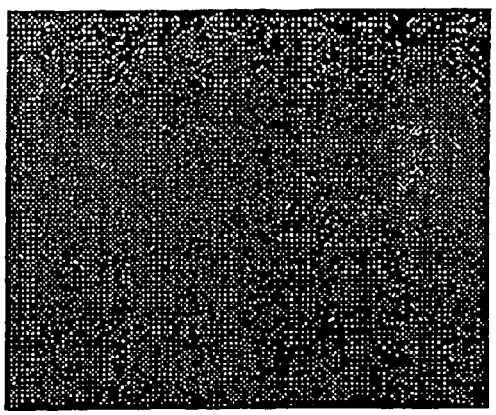
FIG. 5 illustrates fluorescent micrograms for cells differentiated into β cells in Example 9.
Figure 5:
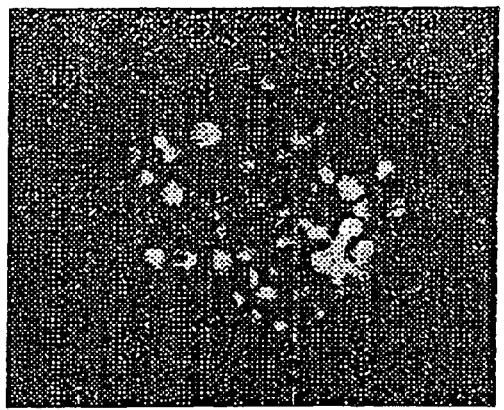
Figure 5:
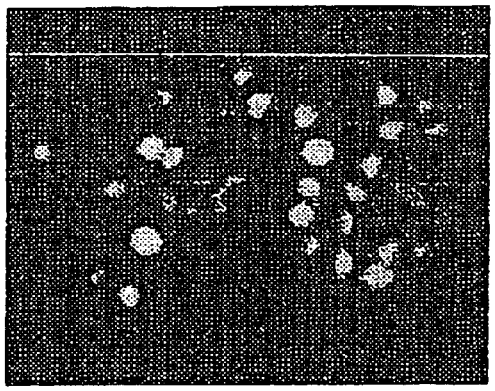
Figure 5:
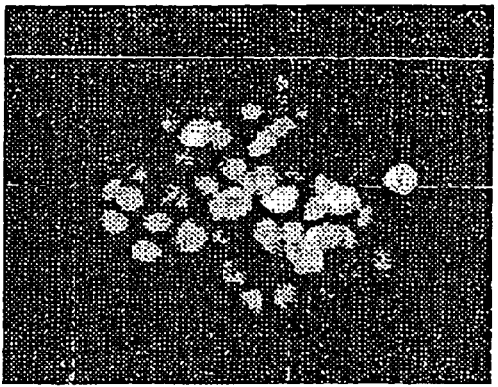

Cells of the AR42J cell line derived from pancreatic cancer induced by chemical carcinogens (Christophe, *Am. J. Physiol.*, 266: G963 (1994)) were suspended to a concentration of $10^5$ cells/mL using Dulbecco's modified Eagle MEM medium containing 10% fetal calf serum and the Met-77 residue betacellulin prepared in Example 3, the Met-76 residue betacellulin prepared in Example 6, or the Met-80 residue betacellulin prepared in accordance with the method in Japanese Unexamined Patent Application (Kokai) H10-191989. 500 μL of these suspensions were inoculated to chamber slides and incubated for 5 days at 37° C. in carbon dioxide gas incubators (5% carbon dioxide gas, 95% air). After 5 days, the cells were washed once with PBS, fixed in 10% formaldehyde, and treated for 5 min with 0.1% Triton X-100. Block Ace (Snow Brand, Japan) was then added for 40 minutes of blocking at room temperature. Anti-insulin antibodies (by Advanced Immunochemicals) diluted with 10% Block Ace were added, and a reaction was performed for 40 minutes at room temperature. 0.1% Triton X-100 was added, the reaction solution was allowed to stand for 5 minutes at room temperature, and the cells were then washed three times with PBS. FITC (fluorescein isothiocyanate) labeled anti-mouse IgG antibodies (Cappel) diluted with 10% Block Ace were added, and a reaction was brought about for 40 minutes. 0.1% Triton X-100 was added, the reaction solution was allowed to stand for 5 minutes, the cells were then washed three times with PBS, and they were then observed under a fluorescent microscope. Stained cells, that is, cells which had differentiated into insulin-producing β cells were found in all cases involving the addition of betacellulin (FIG. 5).

EXAMPLE 10

Construction of Human Placenta Alkaline Phosphatase Gene Expression Vector

The differentiation promoting activity into β cells was also determined using AR42J cells transformed with the vector having alkaline phosphatase which had been ligated as a reporter downstream of the insulin promoter. Specifically, cells which have differentiated into β cells by addition of betacellulin produce alkaline phosphatase. As a result, by assaying the alkaline phosphatase activity, the differentiation promoting activity into β cells can be quantitatively assayed.

Genomic DNA was prepared in the conventional manner from rat tail. The 0.75 kb insulin promoter region was amplified by PCR with a primer RI-1 (5'-AGAGTCAAGGATCCCCCAACCACT-3'; SEQ ID NO: 31) and a primer RI-3 (5'-AGCTGGTCACTT AGGGCTGGGG-3'; SEQ ID NO: 32) based on the base sequence of the well known rat insulin II gene promoter (GenBank: Accession No. J00748) using the genomic DNA as template. PCR was also carried out using primers RI-1Cla (5'-GAATCGATAGAGTCAAGGATCCCCCA-3'; SEQ ID NO: 33) and RI-3Xho (5'-GACTCGAGCTGG TCACTTAGGG-3'; SEQ ID NO: 34) using the PCR product as template. The amplified 0.75 kb DNA fragments were isolated, and the pTB1881 plasmid obtained upon insertion into the pT7 Blue vector (Novagen 69820-1) was used to sequence the base sequence of the cloned fragments, confirming that they were the rat insulin promoter. The pTB1881 plasmid was digested with XhoI-ClaI, giving 0.73 kb DNA fragments (rat insulin promoter). The pTB1330 plasmid for the expression of 2.0 kb cDNA (J. Berger et al., Gene, 66, 1 (1988)) encoding human placenta alkaline phosphatase (PLAP) was digested with XhoI-HindIII. The resulting 2.7 kb DNA fragments (PLAP cDNA, containing an SV40-derived splicing site and polyA addition site, pBR322-derived ori, and ampicillin resistance gene) were isolated, and the aforementioned rat insulin promoter region 0.73 kb XhoI-CaII fragment was ligated by T4 DNA ligase reaction, giving the plasmid pTB1898.

EXAMPLE 11

Construction of PLAP Expression AR42J Cells

The pMCneopolyA plasmid (Stratagene) containing the neor gene of TnS and the PLAP expression plasmid pTB1898 were simultaneously introduced into AR42J cells using the transfection reagent TransIT™-LT1 (Mirus, Pen-Vera Corporation). The plasmid introduced cells were then cultured for 2 days in DMEM supplemented with 10% fetal calf serum, and the culture was then continued in selection medium supplemented with 800 μg/mL G418 (geneticin, Gibco BRL). Clones were isolated by limiting dilution of cells growing with G418 resistance.

Cells of each clone were seeded to 24 well plates and cultured for 4 days with and without the addition of 20 ng/mL Met-80 residue betacellulin. The supernatant was collected and heat treated for 30 minutes at 65° C., and the alkaline phosphatase activity in the media was then assayed. Clones showing increased alkaline phosphatase activity with the addition of 80-residue betacellulin were selected. The results with several clones are given in Table 7 below.

TABLE 7

| | PLAP activity (A 405) | |
|---|---|---|
| Clones | No BTC added | BTC added |
| AR1898-033 | 0.034 | 0.366 |
| AR1898-053 | 0.008 | 0.089 |
| AR1898-0192 | 0.077 | 0.752 |

EXAMPLE 12

Figure 6:
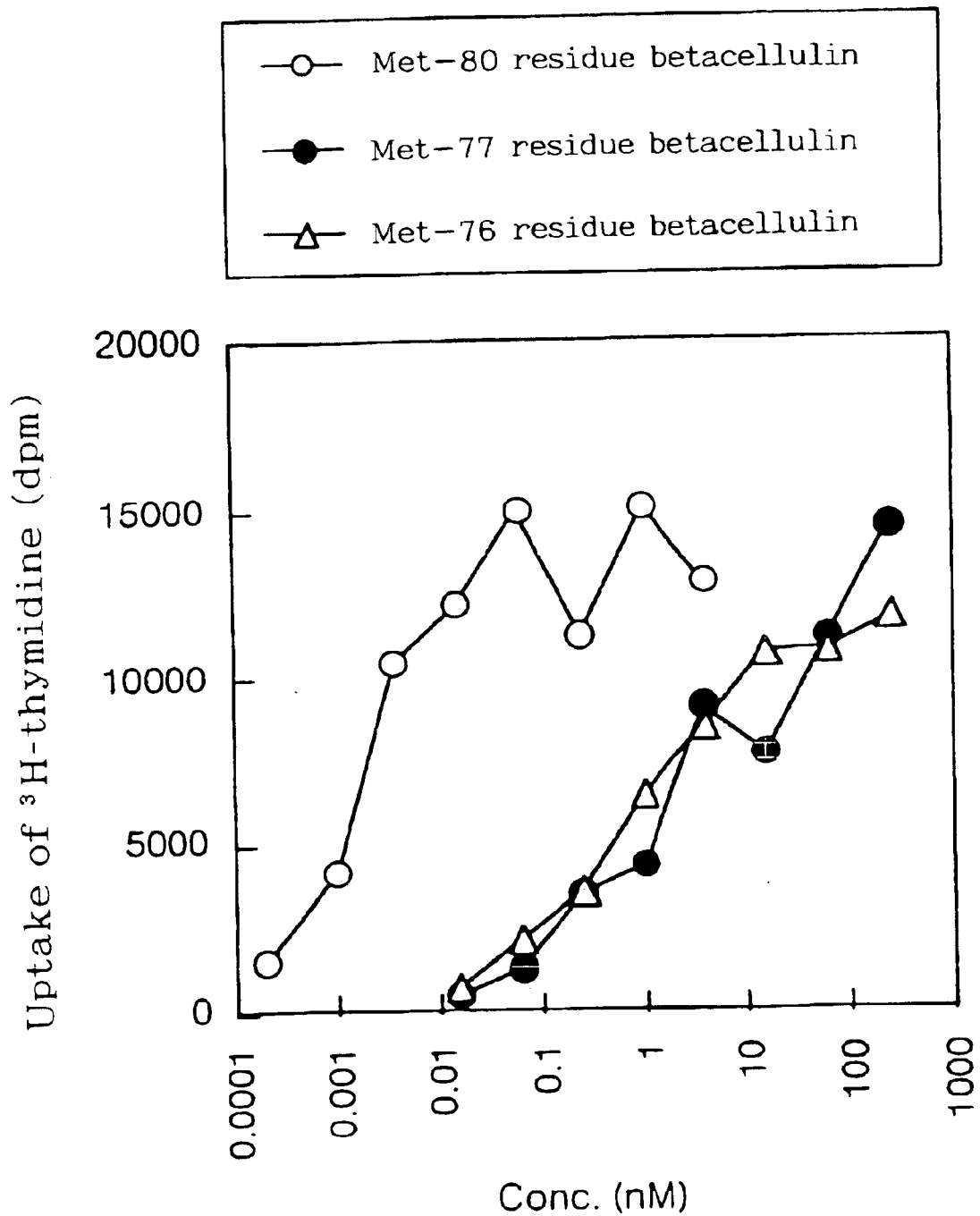
FIG. 6 illustrates the results for β cell differentiation promoting activity in Example 12.

Assay of β Cell Differentiation Promoting Activity Using PLAP Expression AR42J Cells The PLAP expression AR42J cells constructed in Example 11 were suspended to a concentration of $10^5$ cells/mL using Dulbecco's modified Eagle MEM medium containing 10% fetal calf serum and varying concentrations of the Met-77 residue betacellulin prepared in Example 3, the Met-76 residue betacellulin prepared in Example 6, or the Met-80 residue betacellulin prepared in accordance with the method in Japanese Unexamined Patent Application (Kokai) H10-191989. 100 μL of these suspensions were inoculated to 96 well plates and incubated for 5 days at 37° C. in carbon dioxide gas incubators (5% carbon dioxide gas, 95% air). After 5 days, the supernatant was taken and treated for 30 minutes at 65° C., and 50 μL was added to 96-well microplates containing 50 μL of 2×SEAP (2M diethanolamine, 1 mM MgCl$_2$, 20 mM homoarginine). The samples were maintained for 10 minutes at 37° C., 10 μL of 20 mg/mL p-nitrophenylphosphoric acid (Sigma) was then added, and a reaction was brought about for 16 hours at 37° C. (FIG. 6). The Met-77 residue betacellulin and Met-76 residue betacellulin showed virtually the same promoting activity in inducing differentiation as the Met-80 residue betacellulin.

EXAMPLE 13

Figure 7:
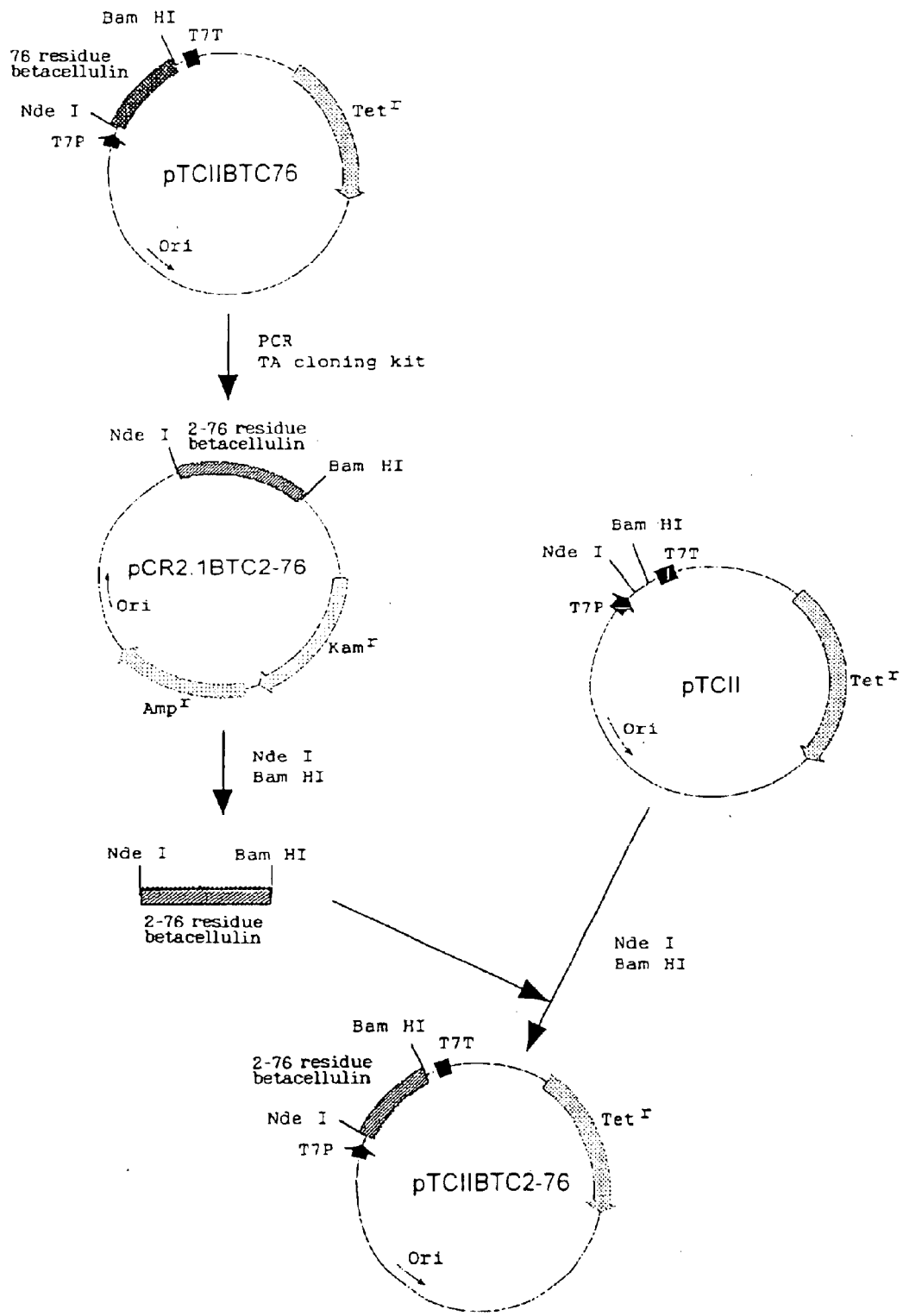
FIG. 7 illustrates the construction of an expression plasmid for 2–76 residue betacellulin (with one N terminal residue and four C terminal residues deleted)

Construction of 2–76 Residue (Lacking one N Terminal Residue and Three C Terminal Residues) Expression Line A 2–76 residue (lacking one N terminal residue and three C terminal residues) betacellulin expression plasmid was constructed in the following manner (FIG. 7).

The 2–76 residue (lacking one N terminal residue and three C terminal residues) betacellulin structural gene was amplified by PCR from the 76-residue (lacking three C terminal residues) betacellulin expression plasmid pTCI-IBTC76 (Example 4) using a primer 3 (5'-CAGCATATGGGGAATTCCACCAGAAGTCCT; SEQ ID NO: 39) having an NdeI cleavage site and start codon adjacent upstream of the glycine at 2 and a primer 4 (5'-GGATCCCTAAACTCTCTCACACCTTGCTCCA ATG; SEQ ID NO: 40) having a stop codon and BamHI cleavage site after the valine of the C terminal. The gene thus amplified by PCR was ligated to the pCR2.1 vector using a TA original cloning kit (by Invitrogen) to prepare pCR2.1BTC2–76. This was introduced to E. coli JM 109, and transformants were selected using ampicilin resistance as an indicator. Transformants having pCR2.1BTC2–76 were cultured, and pCR2. 1BTC2–76 was prepared using a QIAprep8 Miniprep kit (by Qiagen).

The pCR2.1BTC2–76 was digested with NdeI and BamHI for agarose electrophoresis. Approximately 230 bp of the 2–76 residue betacellulin structural gene was recovered using a QIAGEN gel extraction kit (by Qiagen). The expression vector PTCII (Example 1) was digested with NdeI and BamHI for agarose electrophoresis, and approximately 4.6 kbp bands were similarly recovered. The 2–76 residue betacellulin structural gene was ligated with the NdeI-BamHI fragment of the PTCII expression vector and then introduced into E. coli JM109 for selection of transformants by tetracycline resistance, and plasmids were again recovered from the strain, giving the expression plasmid pTCIIBTC2–76.

The resulting pTCIIBTC2–76 was introduced into E. coli MM294 (DE3) for selection of transformants by tetracycline resistance, giving the 2–76 residue betacellulin expression strain MM294 (DE3)/pTCIIBTC2–76.

EXAMPLE 14

Culture of 2–76 Residue Betacellulin Expression Strain

The 2–76 residue betacellulin expression strain MM294 (DE3)/pTCIIBTC2–76 was cultured for 16 hours at 30° C.

in 30 mL of LB medium (1% peptone, 0.5% yeast extract, 0.5% sodium chloride) containing 10 mg/L tetracycline. 10 mL of the resulting culture was used to inoculate each of six 1 L Mayer flask containing 200 mL primary fermentation media (1.68% sodium monohydrogen phosphate, 0.3% sodium dihydrogen phosphate, 0.1% ammonium chloride, 0.05% sodium chloride, 0.012% magnesium sulfate, 0.0007% thiamine hydrochloride, 1.5% glucose, 1.5% Hicase) for stirred culture at 200 rpm and a temperature of 37° C. When the turbidity of the culture reached about 160 Klett units, 5.95 mg/L isopropyl-β-D-thiogalactopyranoside (IPTG) was added. The culture was continued for another four hours after the IPTG had been added. The culture broth was centrifuged for 30 minutes at 9,000 rpm to collect 5.1 g of cells.

EXAMPLE 15

Purification of 2–76 Residue Betacellulin 15 mL of 0.1 M Tris-HCl (pH 8.0) containing 1 mM EDTA, 1 mM APMSF, and 7 M guanidine hydrochloride was added to 5 g of the cells obtained in Example 14, the mixture was stirred over night at 4° C. for extraction, and it was then centrifuged (10 min at 9,000 rpm). 250 mL of 50 mM Tris-HCl (pH 8.0) containing 0.5 mM oxidized type glutathione, 1 mM reduced type glutathione, 1 mM EDTA, 0.1 M arginine hydrochloride, and 2 M urea was added to 15 mL of the resulting supernatant for refolding overnight at 4° C., followed by centrifugation (10 min at 10,000 rpm), resulting in 265 mL of supernatant. 1 L of 2 M urea was added to the supernatant, the pH was then adjusted to 5.0 with acetic acid, and it was allowed to stand over night at 4° C. It was then centrifuged (10 min at 10,000 rpm), the resulting supernatant was adsorbed at a flow rate of 30 mL/min onto a Poros 50HS column (2.2 cm×12 cm, by Nippon Perceptive) equilibrated with 50 mM sodium acetate buffer (pH 5.0), and the column was extensively washed with the buffer used for equilibration, followed by elution with a linear gradient of 0.3 to 1.3 M sodium chloride. Fractions containing the 2–76 residue betacellulin were collected, diluted 3-fold with 50 mM sodium acetate buffer (pH 4.5), and then applied to a TSKgel CM-5PW column (0.75 cm×7.5 cm, by Tosoh) equilibrated with the buffer. Fractions were eluted, from the TSKgel CM-5PW column onto which the 2–76 residue betacellulin had been adsorbed, with a linear gradient of 0.3 to 0.5 M sodium chloride. Fractions containing the 2–76 residue betacellulin were collected and adsorbed to a TSKgel ODS-120T column (2.15 cm×30 cm, by Tosoh) equilibrated with 0.1% trifluoroacetic acid, and the 2–76 residue betacellulin was eluted with a linear gradient of 20 to 44% acetonitrile. The eluate was lyophilized, then dissolved in 5 mL of distilled water, allowed to flow through an AG1-X8 column (1.0 cm×10 cm, by Nippon Biorad) treated with acetic acid, and then again lyophilized, giving 0.7 mg of 2–76 residue betacellulin.

EXAMPLE 16

Figure 8:
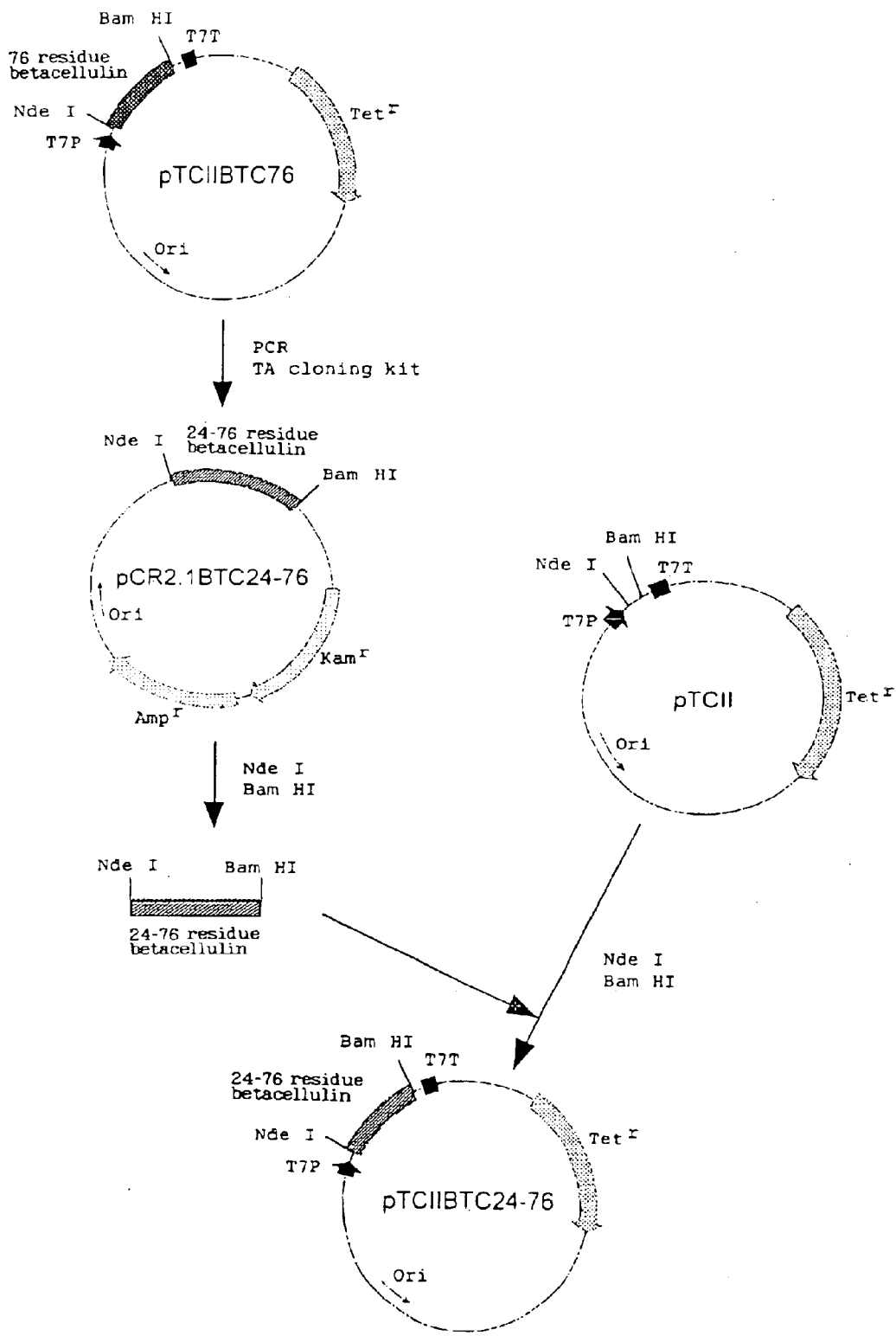
FIG. 8 illustrates the construction of an expression plasmid for 24–76 residue betacellulin (with twenty three N terminal residues and four C terminal residues deleted)

Construction of 24–76 Residue (Lacking 23 N Terminal Residues and Three C Terminal Residues) Expression Strain A 24–76 residue (lacking 23 N terminal residues and three C terminal residues) betacellulin expression plasmid was constructed in the following manner (FIG. 8).

The 24–76 residue (lacking 23 N terminal residues and three residues) betacellulin structural gene was amplified by PCR from the 76-residue (lacking three C terminal residues) betacellulin expression plasmid pTCIIBTC76 prepared in Example 4 using a primer 5 (5'-CAGCATATGGCT ACCACCACACAATCAAAG; SEQ ID NO: 41) having an NdeI cleavage site and start codon adjacent upstream of the alanine at 24 and a primer 4 (5'-GGATCCCTAAAC TCTCTCACACCTTGCTCCAATG; SEQ ID NO: 40) having a stop codon and BamHI cleavage site after the valine of the C terminal. The gene thus amplified by PCR was ligated to the pCR2.1 vector using a TA original cloning kit (by Invitrogen) to prepare pCR2.1BTC24–76. This was introduced to E. coli JM109, and transformants were selected using ampicillin resistance as an indicator. Transformants having pCR2.1BTC24–76 were cultured, and pCR2.1BTC24–76 was prepared using a QIAprep8 Miniprep kit (by Qiagen).

The pCR2.1BTC24–76 was digested with NdeI and BamHI for agarose electrophoresis and approximately 160 bp of the 24–76 residue betacellulin structural gene was recovered using a QIAGEN gel extraction kit (by Qiagen). The expression vector PTCII prepared in Example 1 was digested with NdeI and BamHI for agarose electrophoresis, and approximately 4.6 kbp bands were similarly recovered. The 24–76 residue betacellulin structural gene was ligated with the NdeI-BamHI fragment of the pTCII expression vector and then introduced into E. coli JM109 for selection of transformants by tetracycline resistance, and plasmids were again recovered from the strain, giving the expression plasmid pTCIIBTC24–76.

The resulting pTCIIBTC24–76 was introduced into E. coli MM294 (DE3) for selection of transformants by tetracycline resistance, giving the 24–76 residue betacellulin expression strain MM294 (DE3)/pTCIIBTC24–76.

EXAMPLE 17

Culture of 24–76 Residue Betacellulin Expression Strain

The 24–76 residue betacellulin expression strain MM294 (DE3)/pTCIIBTC24–76 was cultured for 16 hours at 30° C. in 30 mL of LB medium (1% peptone, 0.5% yeast extract, 0.5% sodium chloride) containing 10 mg/L tetracycline. The resulting culture was used to inoculate five 1 L Mayer flask containing 150 mL of primary fermentation media (1.68% sodium monohydrogen phosphate, 0.3% sodium dihydrogen phosphate, 0.1% ammonium chloride, 0.05% sodium chloride, 0.012% magnesium sulfate, 0.0007% thiamine hydrochloride, 1.5% glucose, 1.5% Hicase) for stirred culture at 200 rpm and a temperature of 37° C. When the turbidity of the culture reached about 160 Klett units, 5.95 mg/L isopropyl-β-D-thiogalactopyranoside (IPTG) was added. The culture was continued for another four hours after the IPTG had been added. The culture broth was centrifuged for 30 minutes at 10,000 rpm to collect 3.9 g of cells.

EXAMPLE 18

Purification of 24–76 Residue Betacellulin 12 mL of 0.1 M Tris-HCl (pH 8.0) containing 1 mM EDTA, 1 mM APMSF, and 7 M guanidine hydrochloride was added to the 3.9 g of cells obtained in Example 5, the mixture was stirred over night at 4° C. for extraction, and it was then centrifuged (10 min at 9,000 rpm). 200 mL of 50 mM Tris-HCl (pH 8.0) containing 0.5 mM oxidized type glutathione, 1 mM reduced type glutathione, 1 mM EDTA, 0.1 M arginine hydrochloride, and 2 M urea was added to 12 mL of the resulting supernatant for refolding overnight at 4° C., followed by centrifugation (10 min at 10,000 rpm), resulting in 212 mL of supernatant. 0.8 L of 2 M urea was added to the supernatant, the pH was then adjusted to 5.0 with acetic acid, and it was allowed to stand over night at 4° C. It was then centrifuged (10 min at 10,000 rpm), the resulting supernatant was adsorbed at a flow rate of 30 mL/min onto a Poros SOHS column (2.2 cm×12 cm, by Nippon Perceptive) equilibrated with 50 mM sodium acetate buffer (pH 5.0), and the column was extensively washed with the buffer used for equilibration, followed by elution with a linear gradient of 0.3 to 1.3 M sodium chloride. Fractions containing the 24–76 residue betacellulin were collected, diluted 3-fold with 50 mM sodium acetate buffer (pH 4.5), and then applied to a TSKgel CM-5PW column (0.75 cm×7.5 cm, by Tosoh) equilibrated with the buffer. Fractions were eluted, from the TSKgel CM-SPW column onto which the 24–76 residue betacellulin had been adsorbed, with a linear gradient of 0.3 to 0.5 M sodium chloride. Fractions containing the 24–76 residue betacellulin were collected and adsorbed to a TSKgel ODS-120T column (2.15 cm×30 cm, by Tosoh) equilibrated with 0.1% trifluoroacetic acid, and the 24–76 residue betacellulin was eluted with a linear gradient of 20 to 44% acetonitrile. The eluate was lyophilized, then dissolved in 5 mL of distilled water, allowed to flow through an AG1-X8 column (1.0 cm×10 cm, by Nippon Biorad) treated with acetic acid, and then again lyophilized, giving 0.4 mg of 24–76 residue betacellulin.

EXAMPLE 19

Characterization of Betacellulin Muteins

The 2–76 residue betacellulin mutein obtained in Example 3 and the 24–76 residue betacellulin mutein obtained in Example 6 were characterized in the following manner.

a) Analysis by SDS-PAGE

Figure 9:
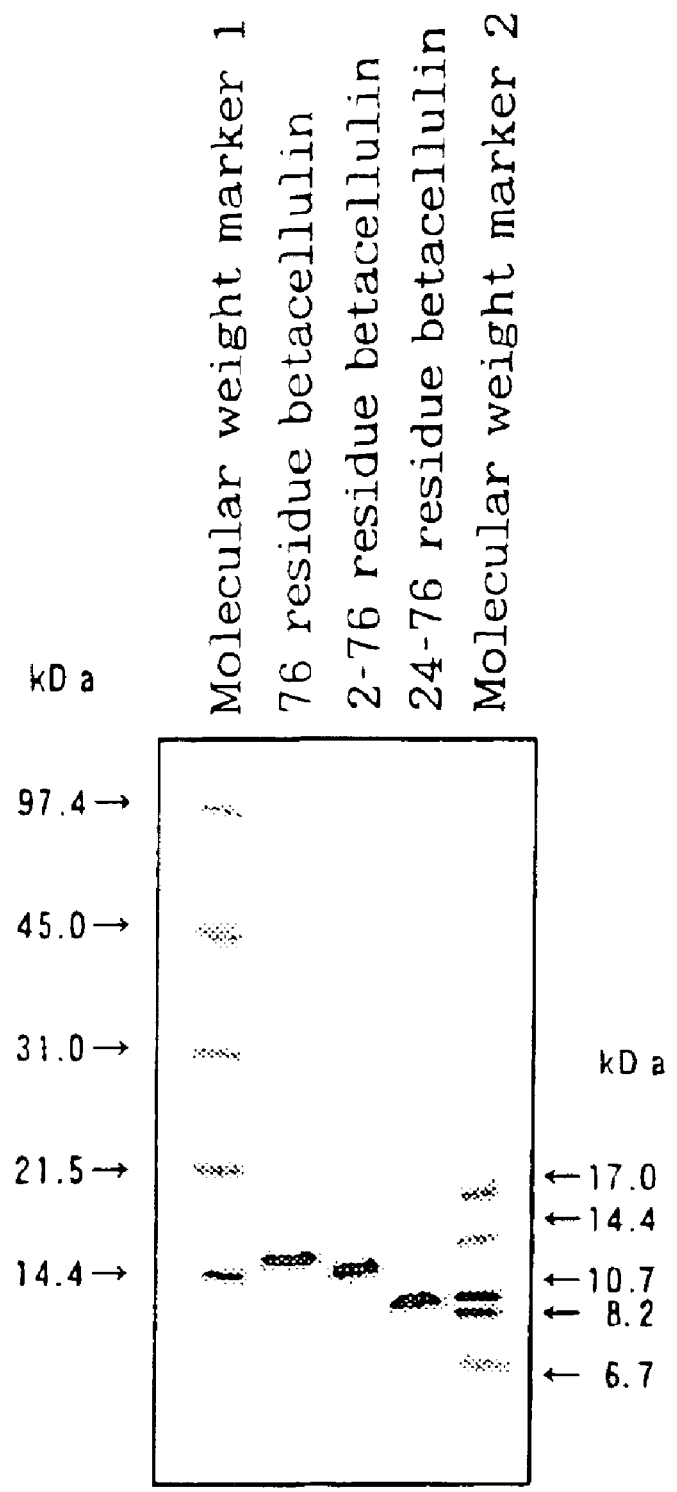
FIG. 9 illustrates the results of gel staining after electrophoresis in Example 19.

The betacellulin muteins and 76 residue betacellulin prepared in Example 6 were suspended in sample buffer (125 mM Tris-HCl, 1% sodium dodecylsulfate, 15% glycerol, 5% 2-mercaptoethanol, 0.005% bromophenol blue), and were electrophoresed on Multigel 15/25 (Dai'ichi Kagaku Yakuhin). Staining of the electrophoresed gel with Rapid CBB Kanto (Kanto Chemical) revealed a single band in virtually all cases (FIG. 9).

b) Analysis of Amino Acid Composition

The betacellulin muteins were hydrolyzed in the gas phase for 24 and 48 hours at 110° C. with 6 N hydrochloric acid containing 4% thioglycolic acid, and the amino acid composition was determined with an amino acid analyzer (Hitachi L-8500A Amino Acid Analyzer). The results showed that both muteins were consistent with the amino acid composition predicted on the basis of the cDNA base sequences (Tables 8 and 9).

TABLE 8 analysis of amino acid composition of 2-76 residue betacellulin

| Amino acid | Number of residues per mol | Theoretical value |
| --- | --- | --- |
| Asx | 5.2 | 5 |
| Thr | 6.0 | 6 |
| Ser | 4.6 | 5 |
| Glx | 9.4 | 9 |

TABLE 8-continued analysis of amino acid composition of 2-76 residue betacellulin

| Amino acid | Number of residues per mol | Theoretical value |
| --- | --- | --- |
| Pro | 4.3 | 4 |
| Gly | 7.3 | 7 |
| Ala | 4.2 | 4 |
| Val | 4.1 | 4 |
| Met | 0.0 | 0 |
| Ile | 2.0 | 2 |
| Leu | 2.0 | 2 |
| Tyr | 2.9 | 3 |
| Phe | 2.1 | 2 |
| Lys | 5.1 | 5 |
| His | 2.3 | 2 |
| Arg | 7.2 | 7 |
| Cys | ND | 8 |

TABLE 9 analysis of amino acid composition of 24-76 residue betacellulin

| Amino acid | Number of residues per mol | Theoretical value |
| --- | --- | --- |
| Asx | 1.0 | 1 |
| Thr | 3.8 | 4 |
| Ser | 2.9 | 3 |
| Glx | 6.0 | 6 |
| Pro | 2.1 | 2 |
| Gly | 4.0 | 4 |
| Ala | 3.0 | 3 |
| Val | 3.9 | 4 |
| Met | 0.0 | 0 |
| Ile | 2.0 | 2 |
| Leu | 0.0 | 0 |
| Tyr | 2.9 | 3 |
| Phe | 2.1 | 2 |
| Lys | 4.9 | 5 |
| His | 2.2 | 2 |
| Arg | 6.0 | 6 |
| Cys | ND | 6 | c) Analysis of N Terminal Amino Acid Sequence

The N terminal amino acid sequence was analyzed using a gas phase protein sequencer (Applied Biosystems, Model 477A). The results showed that both muteins were consistent with the amino acid composition deduced from the cDNA base sequences (Tables 10 and 11).

TABLE 10

Analysis of N terminal amino acid sequence of 2-76 residue betacellulin

| | PTH-amino acid detected (pmole) | Amino acid deduced from base sequence |
| --- | --- | --- |
| 1 | Gly (388) | Gly |
| 2 | Asn (319) | Asn |
| 3 | Ser (245) | Ser |
| 4 | Thr (261) | Thr |
| 5 | Arg (225) | Arg |
| 6 | Ser (144) | Ser |
| 7 | Pro (246) | Pro |
| 8 | Glu (105) | Glu |
| 9 | Thr (120) | Thr |
| 10 | Asn (162) | Asn |

TABLE 11

Analysis of N terminal amino acid sequence of 24-76 residue betacellulin

|   | Detected PTH-amino acid (pmole) | Amino acid predicted based on base sequence |
|---|---|---|
| 1 | Ala (463) | Ala |
| 2 | Thr (251) | Thr |
| 3 | Thr (245) | Thr |
| 4 | Thr (483) | Thr |
| 5 | Gln (302) | Gln |
| 6 | Ser (109) | Ser |
| 7 | Lys (64) | Lys |
| 8 | Arg (145) | Arg |
| 9 | Lys (209) | Lys |
| 10 | Gly (170) | Gly | d) Analysis of C Terminal Amino Acids

The C terminal amino acids were determined using an amino acid analyzer (Hitachi L-8500A Amino Acid Analyzer) by gas phase hydrazinolysis (6 hours at 100° C.). Valine was detected in both muteins (Tables 12 and 13).

TABLE 12

Analysis of C terminal amino acid in 2-76 residue betacellulin

Val (yield: 95.4%)

TABLE 13

Analysis of C terminal amino acid in 24-76 residue betacellulin

Val (yield: 83.3%)

EXAMPLE 20

1) EGF Binding Assay Using A431 Cells

Cell growth promoting activity was assayed by means of the inhibiting activity of binding to $^{125}$I-EGF using human squamous epithelial carcinoma cells A431 (high EGF receptor expression line).

Specifically, 100 μL of A431 cells suspended to a concentration of $10^5$ cells/mL using Dulbecco's modified Eagle MEM (DMEM) medium supplemented with 10% fetal calf serum were inoculated to 96 well plates and cultured for 2 days at 37° C. in carbon dioxide gas incubators (5% carbon dioxide gas and 95% air). After 2 days, the cells were washed 3 times with 200 μL/well of binding medium comprising an equimolar mixture of DMEM and F-12 containing 20 mM HEPES and 0.1% bovine serum albumin, followed by the addition of 100 μL of binding medium comprising varying concentrations of unlabeled EGF, the 2–76 residue betacellulin prepared in Example 15, the 24–76 residue betacellulin prepared in Example 18, the Met-76 residue betacellulin prepared in Example 6, and the Met-80 residue betacellulin prepared in accordance with Japanese Unexamined Patent Application (Kokai) H10–191989 and 0.25 nM $^{125}$I-EGF (Amersham Pharmacia Biotech). The mixtures were allowed to stand for 90 minutes at 4° C., and then washed 3 times with 200 μL of binding medium, and the cells were lysed in 200 μL of 0.1 N sodium hydroxide aqueous solution containing 1% SDS. The cell lysate was then transferred to scintillation vials, 1 mL of Scintillator A (Wako Pure Chemicals) was added, and the inhibiting activity of binding to $^{125}$I-EGF was assayed with a scintillation counter.

2) Assay of β Cell Differentiation Promoting activity using human placenta alkaline phosphatase expression AR42J cells PLAP expression AR42J cells were suspended to a concentration of $10^5$ cells/mL using Dulbecco's modified Eagle MEM medium containing 10% fetal calf serum and varying concentrations of the 2–76 residue betacellulin prepared in Example 15, the 24–76 residue betacellulin prepared in Example 18, the Met-76 residue betacellulin prepared in Example 6, or the Met-80 residue betacellulin prepared in accordance with Japanese Unexamined Patent Application (Kokai) H10-191989. 100 μL of these suspensions were inoculated to 96 well plates and incubated for 5 days at 37° C. in carbon dioxide gas incubators (5% carbon dioxide gas, 95% air). After 5 days, the culture supernatant were treated for 30 minutes at 65° C., and 50 μL was then added to 96-well microplates containing 50 μL of 2×SEAP (2M diethanolamine, 1 mM $MgCl_2$, 20 mM homoarginine). 10 μL of 20 mg/mL p-nitrophenylphosphoric acid (Sigma) was added, and a reaction was brought about for 16 hours at 37° C. The ratio between EGF activity and the BTC activity of all the muteins decreased to about 5% of that of the Met-80 residue betacellulin, and was about the same as that of the Met-76 residue betacellulin, with no apparent influence by the N terminal deletion.

3) The results of 1) and 2) above are summarized in Table 14.

TABLE 14

|  | BTC activity $EC_{50}$ (nM) | EGF activity $IC_{50}$ (nM) | EGF/BTC relative to Met-BTC80 |
|---|---|---|---|
| Met-BTC80 | 0.07 | 1.2 | 100.0% |
| Met-BTC76 | 0.30 | 95.1 | 5.4% |
| BTC2-76 | 0.12 | 38.6 | 5.3% |
| BTC24-76 | 0.03 | 11.0 | 4.7% |

EXAMPLE 21

Construction of hBTC50 Mutein A Expression Plasmid pTB1985 Incorporating 3 Heregulin (Her)-derived Residues Between Cys3-Cys4

PCR was carried out with pTB1976 as template using (1) a 5' side primer PET -1 (5'-GAAATAATTTTG TTTAACTTTAAGAAGGAG-3'; SEQ ID NO: 52) and a 3' side primer BTC-1 (5'-AGGAGGGCGTCGAGG GGTTCTGCTCGGCCA-3'; SEQ ID NO: 53) and (2) 5' side primer BTC-2 (5'-TGGCCGAGCAGAACCCCT CGACGCCCTCCT-3'; SEQ ID NO: 54) and a 3' side primer BTC-3 (5'-TCTATGCGCACCCGTTCTCGGAGC ACTGTC-3'; SEQ ID NO: 55).

A mixture of the PCR products of (1) and (2) was used as template for PCR using a 5' side primer BT-95h (SEQ ID NO: 50) and a 3' side primer BT-94h (SEQ ID NO: 51), giving DNA fragments encoding mutein A with 3 amino acids (Asn, Pro, Ser) of the Her sequence inserted between the Cys3-Cys4 of hBTC50. The DNA fragment was digested with NdeI and BamHI, and then inserted into the NdeI-BamHI position of pET-3c to prepare pTB1985.

EXAMPLE 22

Construction of hBTC50 Mutein B Expression Plasmid pTB1987 With Seven N Terminal Residues Substituted by Five Residues of Epithelial Growth Factor (EGF) in the Corresponding Positions pTB1976 was used as template in PCR using a 5' side primer BTC-7 (5'-TATACATATGAACAGCGACTC TGAGTGCCCCAAGC-3'; SEQ ID NO: 56) and the 3' side primer BT-94h (SEQ ID NO: 51), giving DNA fragments encoding mutein B in which seven N terminal residues of hBTC50 were substituted with five corresponding EGF residues. The DNA fragment was digested with NdeI and BamHI, and then incorporated into the NdeI-BamHI position of pET-3c to prepare pTB1987.

EXAMPLE 23

Expression in *E. coli*

The pTB1976 plasmid, pTB1985 plasmid, and pTB1987 prepared in the following reference examples and above examples were introduced into *E. coli* BL21(DE3)pLysS (Novagen) for expression under the control of the Φ10 promoter of the T7 phage. The various *E. coli* recombinants were cultured at 37° C. using LB medium containing 100 μg/mL ampicillin and 10 μg/mL chloramphenicol. When the turbidity reached 160 Klett units, isopropyl β-D-thiogalactopyranoside was added to a final concentration of 0.4 mM, and the culture was continued for another 4 hours at 37° C. Cells were harvested by centrifugation and stored at −80° C. until extraction.

EXAMPLE 24

Purification of hBTC50, Mutein A and Mutein B 4-1) Preparation of *E. coli* Inclusion Bodies Cells harvested from 400 mL of culture broth were suspended in 20 mL of 10 mM Tris-HCl (pH 8.0), 10% sucrose, and 10 mM EDTA, followed by freezing and thawing. The cells were then allowed to stand for 30 minutes in ice and were completely lysed. They were disrupted by ultrasonication (3 times for 10 sec) while cooled on ice and then centrifuged (15 min at 9000 rpm and a temperature of 4° C.; Beckman), and the precipitate was again collected. These washing operations were repeated three times to prepare inclusion bodies.

4-2) Protein Extraction and Refolding

The inclusion bodies prepared in 4-1) were suspended in 8 mL of 7M guanidine-HCl, 0.1 M Tris-CH$_3$COOH (pH 8.0), and 1 mM EDTA, and they were gently stirred with a stirrer for 1 hour at 4° C. to extract the recombinant protein. Reduced type glutathione was added to 0.1 M, the pH was adjusted to 8.4 with NaOH solution, and nitrogen gas was blown into the extract to displace the air. The extract was allowed to stand for 2 hours at room temperature, and was then diluted with 20 volumes of 10 mM Tris-CH$_3$COOH (pH 8.0), 0.5 mM phenylmethylsufonyl fluoride, and 1 mM benzamidine. The diluted extract was centrifuged (9000 rpm, 15 min, 25° C.) to remove the insoluble material, oxidized type glutathione was added to a concentration of 0.5 mM to the supernatant, and the solution was allowed to stand for 16 hours at room temperature. The supernatant (9000 rpm, 15 min, 25° C.) was lyophilized and concentrated, and then dialyzed (Spectrapor: MWCO 1,000) against 50 mM Tris-CH$_3$COOH (pH 5.5) and 1 mM EDTA at 4° C. After the dialysis, the supernatant (9000 rpm, 15 min, 4° C.) was filtrated with an acetate cellulose membrane (Millex GV, 0.22 μm: Millipore) to remove the insoluble material.

4-3) Purification of Protein

Solution containing refolded protein was loaded on a cation exchange HPLC column (250×4.1 mm. I.d., Synchrom CM300, Synchropak) equilibrated with 50 mM sodium acetate (pH 5.5), and was eluted with a 0 to 1 M NaCl gradient to obtain fractions. Eluted fractions observed at OD$_{280}$ were loaded on a C$_4$ reverse HPLC column (150×4.6 mm I.d., Ultron 300 C$_4$: Chromatopacking Center) equilibrated with 0.1% HCl and 1% CH$_3$CN, and were eluted with a 1 to 40% CH$_3$CN gradient. The peak fractions obtained by column chromatography were then lyophilized. The yields of Muteins A and B were 78.7 and 103.1 μg, respectively.

4-4) Determination of Protein Purity

To determine the purity of the purified product, the product was loaded on a C$_{18}$ reverse phase HPLC column (150×4.6 mm i.d., ODS120T, Tosoh), and was eluted with a 15 to 30% CH$_3$CN gradient, confirming the identity of the peak proteins of Muteins A and B. Both proteins had a purity of 94% or more.

EXAMPLE 25

Assay of Cell Growth Promoting Activity Using 3T3 Cells

The cell growth promoting activity was assayed by means of the $^3$H-thymidine uptake into stationary 3T3 A31-714 Clone 4 (*International Journal of Cancer*, 12:463 (1973)) as described in *Molecular Cell Biology*, 8:588 (1988).

100 μL 3T3 A31-714 Clone 4 suspended to 1000 cells/mL using Dulbecco's modified Eagle MEM medium containing 5% bovine serum were seeded to 96 well plates and cultured for a day at 37° C. in carbon dioxide gas incubators (5% carbon dioxide gas, 95% air). 75 μL of supernatant was taken, and 100 μL of serum-free Dulbecco's modified Eagle MEM medium was added to adjust the serum concentration to 1%. Two more days of culture was followed by the addition of varying concentrations of the hBTC50, Mutein A, or Mutein B prepared in the above examples. 16 hours after these had been added, $^3$H-thymidine (Amersham Pharmacia Biotech) was added in an amount of 0.25 μCi/well, after 4 hours the cells were washed 3 times with PBS, 100 μL of 5% SDS was added, and the cells were lysed. The cell lysate was transferred to scintillation vials, 1 mL of Scintillator A (Wako Pure Chemicals) was added, and the uptake of $^3$H-thymidine into the cellwas assayed with a scintillation counter.

Table 15 gives the results of the concentrations of hBTC50 and the muteins showing 50% activity (ED$_{50}$), where 100% is the maximum uptake of the 80-residue betacellulin (reference).

TABLE 15

| cell growth promoting activity | |
|---|---|
| Sample | ED$_{50}$ (nM) |
| hBTC50 | 0.01 |
| Mutein A | 0.6 |
| Mutein B | >10.0 |

EXAMPLE 26

Assay of β Cell Differentiation Promoting Activity Using AR42J Cells

Cells of the AR42J cell line derived from pancreatic cancer induced by chemical carcinogens (Christophe, *Am. J. Physiol.*, 266: G963 (1994)) were suspended to a concentration of 10$^5$ cells/mL in Dulbecco's modified Eagle MEM medium containing 10% fetal calf serum and one of hBTC50, Mutein A, Mutein B, or the 80-residue betacellulin (hBTC80) prepared in accordance with the method in Japanese Unexamined Patent Application (Kokai) H10-191989. 500 μL of these suspensions was inoculated on chamber slides and incubated for 5 days at 37° C. in carbon dioxide gas incubators (5% carbon dioxide gas, 95% air). After 5 days, the cells were washed once with PBS, fixed in 10% formaldehyde, and treated for 5 min with 0.1% Triton X-100. Block Ace (Snow Brand, Japan) was then added for 40 minutes of blocking at room temperature. Anti-insulin antibodies (by Advanced Immunochemicals) diluted with 10% Block Ace were added, and reacted for 40 minutes at room temperature. 0.1% Triton X-100 was added, the reaction solution was allowed to stand for 5 minutes at room temperature, and the cells were then washed three times with PBS. FITC (fluorescein isothiocyanate) labeled anti-mouse IgG antibodies (Cappel) diluted with 10% Block Ace were added, and a reaction was brought about for 40 minutes. 0.1% Triton X-100 was added, the reaction solution was allowed to stand for 5 minutes, the cells were then washed three times with PBS, and they were then observed under a fluorescent microscope.

Stained cells, that is, cells which had differentiated into insulin-producing β cells, were found in all cases involving the addition of hBTC50 and Muteins A and B, as was the case when hBTC80 was added.

There were no differences in the incidence of insulin-producing cells between hBTC80, hBTC50, and Muteins A and B.

EXAMPLE 27

Assay of β Cell Differentiation Promoting Activity Using PLAP Expression AR42J Cells 3-1) Construction of Human Placenta Alkaline Phosphatase Gene Expression Vector The differentiation promoting activity into β cells was also determined using AR42J cells transformed with the vector having alkaline phosphatase which had been ligated as a reporter downstream of the insulin promoter. Specifically, cells which have differentiated into β cells by addition of betacellulin produce alkaline phosphatase. As a result, by assaying the alkaline phosphatase activity, the differentiation promoting activity into β cells can be quantitatively assayed.

Genomic DNA was prepared in the conventional manner from rat tail. The 0.75 kb insulin promoter region was amplified by PCR with a primer RI-1 (5'-AGAGTCAAGGATCCCCCAACCACT-3'; SEQ ID NO: 31) and a primer RI-3 (5'-AGCTGGTCACTTAGG GCTGGGG-3'; SEQ ID NO: 32) based on the base sequence of the well known rat insulin II gene promoter (GenBank: Accession No. J00748) using the genomic DNA as template. PCR was also carried out using primers RI-1Cla (5'-GAATCGATAGAGTCAAGGATCCCCCA-3'; SEQ ID NO: 33) and RI-3Xho (5'-GACTCGAGCTGGTCACTTA GGG-3'; SEQ ID NO: 34) using the PCR product as template. The amplified 0.75 kb DNA fragments were isolated, and the pTB1881 plasmid obtained upon insertion into the pT7 Blue vector (Novagen 69820-1) was used to sequence the base sequence of the cloned fragments, confirming that they were the rat insulin II promoter. The pTB1881 plasmid was digested with XhoI-ClaI, giving 0.73 kb DNA fragments (rat insulin promoter). The pTB1330 plasmid for the expression of 2.0 kb cDNA (J. Berger et al., *Gene*, 66, 1 (1988)) encoding human placenta alkaline phosphatase (PLAP) was digested with XhoI-HindIII. The resulting 2.7 kb DNA fragments (PLAP cDNA, containing an SV40-derived splicing site and polyA addition site, pBR322-derived ori, and ampicillin resistance gene) were isolated, and the aforementioned rat insulin promoter region 0.73 kb XhoI-ClaI fragment was ligated by T4 DNA ligase reaction, giving the plasmid pTB1898.

3-2) Construction of PLAP Expression AR42J Cells

The pMCneopolyA plasmid (Stratagene) containing the neor gene of Tn5 and the PLAP expression plasmid pTB1898 were simultaneously introduced into AR42J cells using the transfection reagent TransIT™-LT1 (Mirus, Pen-Vera Corporation). The incorporated cells were then cultured for 2 days in DMEM supplemented with 10% fetal calf serum, and the culture was then continued in selection medium supplemented with 800 μg/mL G418 (geneticin, Gibco BRL). Clones were isolated by limiting dilution of cells growing with G418 resistance.

Cells of each clone were seeded on 24-well plates and cultured for 4 days with and without the addition of 20 ng/mL 80-residue BTC, the supernatant was collected and heat treated for 30 minutes at 65° C., and the alkaline phosphatase activity in the media was then assayed. Clones showing increased alkaline phosphatase activity with the addition of 80-residue betacellulin were selected. The AR71-104 clone was used below.

3-3) Assay of β cell Differentiation Promoting Activity Using PLAP Expression AR42J Cells PLAP expression AR42J cells constructed in 3-2) were suspended to a concentration of $3 \times 10^4$ cells/mL in Dulbecco's modified Eagle MEM medium containing 10% fetal calf serum and on of varying concentrations of the hBTC50 or Mutein A or B prepared above. 100 μL of these suspensions were inoculated on 96-well plates and incubated for 5 days at 37° C. in carbon dioxide gas incubators (5% carbon dioxide gas, 95% air). After 5 days, samples of the culture supernatant were treated for 30 minutes at 65° C., and 50 μL was then added to 96-well microplates containing 50 μL of 2×SEAP (2M diethanolamine, 1 mM $MgCl_2$, 20 mM homoarginine). The samples were held for 10 minutes at 37° C., and 10 μL of 20 mg/mL p-nitrophenylphosphoric acid (Sigma) was added, a reaction was brought about for 16 hours at 37° C., and the absorbance at 405 nm ($A_{405}$) was determined.

Table 16 gives the protein concentration ($ED_{50}$) necessary to show 50% activity, where 100% is the maximum absorbance when hBTC50 was added.

TABLE 16

| activity inducing differentiation to β cells | |
|---|---|
| Sample | $ED_{50}$ (nM) |
| hBTC50 | 0.15 |
| Mutein A | 0.5 |
| Mutein B | 0.7 |

REFERENCE EXAMPLE 1

Construction of 50-residue Human Betacellulin (hBTC50) Expression Plasmid pTB1976

The pTB1516 plasmid incorporating the cDNA of 80-residue hBTC (Japanese Unexamined Patent Application (Kokai) H6-87894; Accession No. FERM BP-3836, Accession No. IFO 15282) was used as template in PCR using the BT-95h primer (5'-AGCATATGCGGAAAGGCC ACTTCTCTAGGT-3'; SEQ ID NO: 50) and the BT-94h primer (5'-CTGGATCCTAGTAAAACAAGT CAACTCTCT-3'; SEQ ID NO: 51). PCR products with a translation start codon and NdeI site in the 5' terminal of the C terminal 50-residue type hBTC, and a stop codon and a BamHI site inserted at the 3' terminal, were digested with NdeI and BamHI, and were inserted using the DNA Ligation Kit Ver. 2 (Takara) to the NdeI-BamHI site of the pET-3c expression plasmid (Novagen) having the Φ10 promoter of the T7 phage, so as to prepare the pTB1976 plasmid for the expression of hBTC50. The base sequence of the inserted cDNA was confirmed by an ABI DNA sequencer (ABI377 DNA Sequencer).

Figure 10:
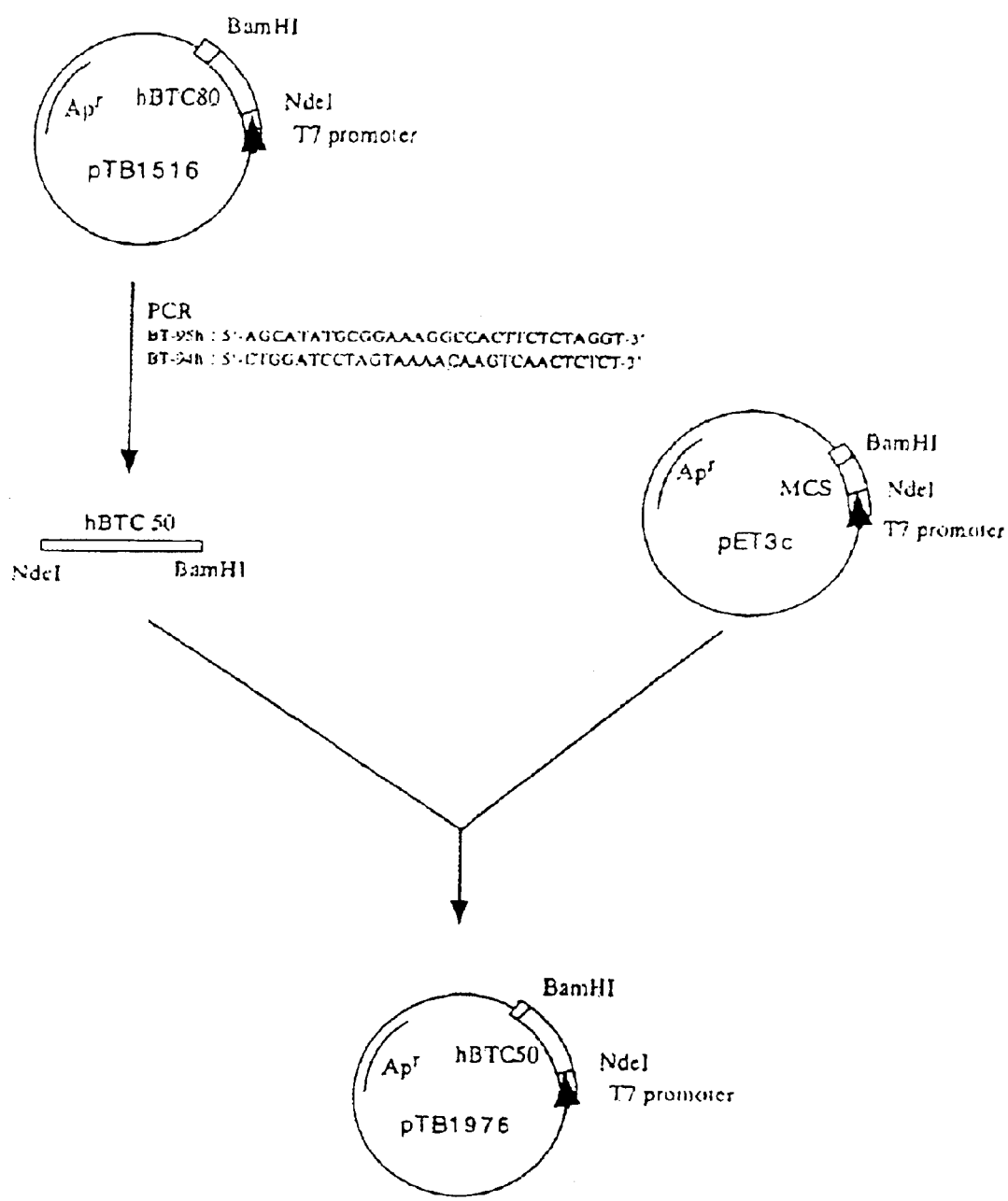
FIG. 10 is a schematic of the construction of the pTB1976 plasmid. The BT-95h primer (upper sequence) is set forth as SEQ ID NO:50. The BT-94h primer (lower sequence) is set forth as SEQ ID NO:51.

FIG. 10 is a schematic of the construction of the pTB1976 plasmid.

Industrial Applicability

The betacellulin muteins and their salts of the present invention have reduced egf activity and intact BTC activity, with no antigenicity-related problems. They are thus useful as better therapeutic drugs for diabetes.

---

What is claimed is:

1. A betacellulin mutein or a salt thereof consisting of the amino acid sequence represented by SEQ ID NO: 38.

2. A betacellulin mutein or salt thereof according to claim 1, wherein the ratio of the pancreatic β cell differentiation promoting activity to the epithelial cell growth promoting activity is at least twice relative to that of betacellulin.

3. A method for manufacturing a betacellulin mutein or salt thereof according to claim 1, characterized by culturing the transformants which have been transformed with recombinant vectors containing DNA encoding the betacellulin mutein according to claim 1 to produce said betacellulin mutein.

4. A pharmaceutical composition comprising a betacellulin mutein or salt thereof according to claim 1.

5. A method for treatment for diabetes, characterized in that a betacellulin mutein or salt thereof according to claim 1 is administered to mammals.

6. The betacellulin mutein or a salt thereof according to claim 1, wherein the mutein has the pancreatic β cell differentiation promoting activity and the reduced epithelial cell growth promoting activity.

* * * * *